US 6,180,759 B1

(12) United States Patent
Mencel et al.

(10) Patent No.: US 6,180,759 B1
(45) Date of Patent: Jan. 30, 2001

(54) PROCESS FOR THE PREPARATION OF AZACYCLOALKYLAKANOYL PSEUDOTETRAPEPTIDES

(75) Inventors: James J. Mencel, Lansdale, PA (US); Robert Stammler; Christophe Daubie, both of Paris (FR); Michel Lavigne, Chilly-Mazarin (FR); Benoit J. Vanasse, Collegeville, PA (US); Robert C. Liu, Walnut Creek, CA (US); Patrick Leon, Tassin la Demi Lune (FR); Geoffrey A. D'Netto; Adam W. Sledeski, both of Collegeville, PA (US)

(73) Assignee: Aventis Pharmaceuticals Products Inc., Bridgewater, NJ (US)

( * ) Notice: Under 35 U.S.C. 154(b), the term of this patent shall be extended for 0 days.

(21) Appl. No.: 09/544,680

(22) Filed: Apr. 7, 2000

Related U.S. Application Data

(63) Continuation of application No. PCT/US98/21326, filed on Oct. 9, 1998.
(60) Provisional application No. 60/061,719, filed on Oct. 10, 1997, now abandoned.

(51) Int. Cl.[7] ............................ C07C 227/18; C07K 1/02; C07K 1/06; C07K 5/02; C07K 5/075
(52) U.S. Cl. ..................... 530/330; 530/332; 530/338; 546/185; 546/233; 546/247; 560/40; 562/443; 562/507; 564/152; 564/153; 564/157
(58) Field of Search .................................. 530/330, 331, 530/332, 338, 339; 546/185, 233, 238, 247, 248, 341; 560/40; 562/443, 507; 564/152, 153, 157

(56) References Cited

U.S. PATENT DOCUMENTS

| 4,870,183 | * | 9/1989 | Iizuka et al. ............... 546/210 |
| 5,663,297 | * | 9/1997 | Alig et al. .................. 530/331 |
| 5,780,590 | * | 7/1998 | Klein et al. ................. 530/331 |

FOREIGN PATENT DOCUMENTS

95/10295 * 4/1995 (WO) .
98/07696 * 2/1998 (WO) .

OTHER PUBLICATIONS

Roberts et al. Basic Principles Of Organic Chemistry, Second Edition. Menlo Park: W. A. Benjamin, Inc. pp. 1072–1073, 1236–1239, 1977.*

* cited by examiner

Primary Examiner—Jeffrey E. Russel
(74) Attorney, Agent, or Firm—Irving Newman

(57) ABSTRACT

This invention is directed to a process for preparing a pseudotetrapeptide of formula I

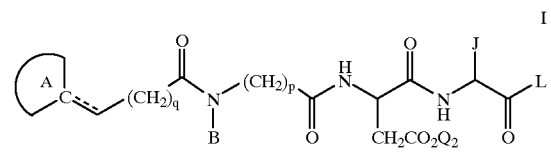

or a salt or prodrug thereof wherein

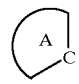

is optionally nitrogen protected azaheterocyclyl;

----- is a single or double bond; q is 1–5; B is alkyl, cycloalkyl, cycloalkylalkyl, alkylcycloalkyl, alkylcycloalkylalkyl, aryl, aralkyl, alkylaryl, or alkylaralkyl; $Q_2$ is H or a carboxylic acid protecting group; J is —H, alkyl, cycloalkyl, cycloalkylalkyl, alkylcycloalkyl, alkylcycloalkylalkyl, aryl, substituted aryl, aralkyl, substituted aralkyl; L is $OR^1$, or $NR^1R^2$, where $R^1$ and $R^2$ are independently —H, alkyl, cycloalkyl, cycloalkylalkyl, alkylcycloalkyl, alkylcycloalkylalkyl, aryl, aralkyl, alkylaryl or alkylaralkyl; and p is 1 or 2 which comprises the coupling of two dipeptides or psuedopeptides.

57 Claims, No Drawings

PROCESS FOR THE PREPARATION OF AZACYCLOALKYLAKANOYL PSEUDOTETRAPEPTIDES

CROSS REFERENCE TO RELATED APPLICATIONS

This is a continuation of International Patent Application No. PCT/US98/21326, filed Oct. 9, 36 1998, which, in turn, claims the benefit of U.S. patent application Ser. No. 60/061,719, filed Oct. 10, 1997, now abandoned.

FIELD OF THE INVENTION

This invention is directed to a process for convergently preparing azacycloalkanoylpseudotetrapeptides comprising coupling a dipeptide with a psuedodipeptide. This invention is also directed to intermediates and processes for preparing the intermediates useful in preparing the pseudotetrapeptide.

BACKGROUND OF THE INVENTION

Azacycloalkylalkanoyl pseudotetrapeptides, as exemplified by N-[N-[N-(4-piperdin-4-yl)butanoyl)-N-ethylglycyl]-(L)-aspartyl]-(L)-β-cyclohexyl-alanine amide, have antithrombotic activity, including the inhibition of platelet aggregation and thrombus formation in mammals, and are useful in the prevention and treatment of thrombosis associated with disease states such as myocardial infarction, stroke, peripheral arterial disease and disseminated intravascular coagulation. See PCT Patent Application Publication No. WO95/10295.

These pseudotetrapeptides have heretofore been prepared by sequential synthesis from the C-terminal amino acid using standard solid phase or solution phase peptide synthesis procedures. However, sequential coupling of amino acids is less desirable for the production of bulk drug as it constrains manufacturing to a linear schedule.

Thus, an alternative preparative approach to the pseudotetrapeptides is needed. Such an approach should substantially increase production versatility and efficiency. A convergent approach should provide for specialized modifications of the pseudotetrapeptide by performing specialized chemistry on one of the synthons rather than on the whole pseudotetrapeptide, and should provide for the simultaneous preparation of a number of pseudotetrapeptide analogs.

SUMMARY OF THE INVENTION

This invention is directed to a process for the preparation of a pseudotetrapeptide of formula I

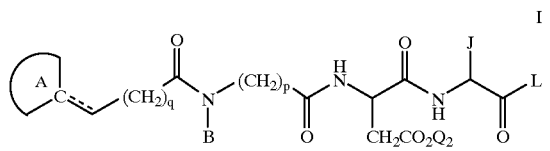

or a salt or prodrug thereof
wherein

is optionally N-protected azaheterocyclyl;

----- is a single or double bond;
q is 1–5;
B is alkyl, cycloalkyl, cycloalkylalkyl, alkylcycloalkyl, alkylcycloalkylalkyl, aryl, aralkyl, alkylaryl, or alkylaralkyl;
$Q_2$ is H or a carboxylic acid protecting group;
J is —H, alkyl, cycloalkyl, cycloalkylalkyl, alkylcycloalkyl, alkylcycloalkylalkyl, aryl, substituted aryl, aralkyl or substituted aralkyl;
L is $OR^1$, or $NR^1R^2$, where $R^1$ and $R^2$ are independently —H, alkyl, cycloalkyl, cycloalkylalkyl, alkylcycloalkyl, alkylcycloalkylalkyl, aryl, aralkyl, alkylaryl, or alkylaralkyl; and
p is 1 or 2,
comprising
(a) coupling a azabeterocyclyl pseudodipeptide of formula

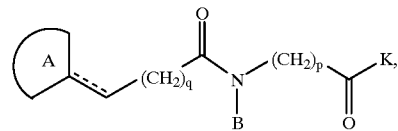

or a salt thereof wherein K is OH or an acyl activating group,
with a carboxylic acid substituted dipeptide of formula

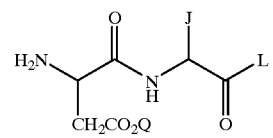

or a salt thereof,
(b) optionally removing the nitrogen protecting group or carboxylic acid protecting group to prepare the pseudotetrapeptide, and
(c) optionally converting the pseudotetrapeptide to the salt or prodrug.

DETAILED DESCRIPTION OF THE INVENTION

Definitions of Terms

As used above, and throughout the description of this invention, the following terms, unless otherwise indicated, shall be understood to have the following meanings:

"Azaheterocyclyl" means a 4–8 membered saturated, unsaturated, or aromatic carbocyclic ring system in which one of the carbon atoms other than the carbon of the

moiety is replaced with a nitrogen atom. When the nitrogen atom is incorporated in the ring system through two single bonds, it is optionally substituted by a nitrogen protecting group $P_1$. Representative azaheterocyclyl groups include piperidinyl, N-tert-butoxycarbonylpiperidinyl, N-benzyloxycarbonypiperidinyl, pyrrolidinyl, N-tert-butoxycarbonylpyrrolidinyl, N-benzyloxycarbonypyrolidinyl, pyrrolyl, pyridinyl, and the like. Preferred azaheterocyclyl groups are pyridyl, N-tert-butoxycarbonylpiperidin-4-yl and N-benzyloxycarbonypiperidin-4-yl.

"Alkyl" means a saturated aliphatic hydrocarbon group, which may be straight or branched, having about 1 to about 20 carbon atoms in the chain. Branched means that a lower alkyl group such as methyl, ethyl or propyl is attached to a linear alkyl chain. Preferred straight or branched alkyl groups are the "lower alkyl" groups which are those alkyl groups having from 1 to about 10 carbon atoms. More preferred lower alkyl groups have from 1 to about 6 carbon atoms.

"Cycloalkyl" means a saturated carbocyclic group having one or more rings and having about 3 to about 10 carbon atoms. Preferred cycloalkyl groups include cyclopropyl, cyclobutyl, cyclopentyl, cyclohexyl, cycloheptyl, and decahydronaphthyl.

"Cycloalkylalkyl means an alkyl group substituted with a cycloalkyl group. Preferred cycloalkylalkyl groups include cyclopentylmethyl, cyclohexylmethyl, cyclohexylethyl, decahydronaphth-1-ylmethyl and decahydronaphth-2-ylmethyl.

"Alkylcycloalkyl" means a cycloalkyl group substituted with an alkyl group. Exemplary alkylcycloalkyl groups include 1-, 2-, 3-, or 4- methyl or ethyl cyclohexyl.

"Alkylcycloalkylalkyl" means an alkyl group substituted by an alkylcycloalkyl group. Exemplary alkylcycloalkyl groups include 1-, 2-, 3-, or 4- methyl or ethyl cyclohexylmethyl or 1-, 2-, 3-, or 4- methyl or ethyl cyclohexylethyl.

"Aryl" means a phenyl or naphthyl group.

"Substituted aryl" means a phenyl or naphthyl group substituted by one or more aryl group substituents which may be the same or different, where "aryl group substituent" includes alkyl, alkenyl, alkynyl, aryl, aralkyl, hydroxy, alkoxy, aryloxy, aralkoxy, hydroxyalkyl, acyl, formyl, carboxy, alkenoyl, aroyl, halo, nitro, trihalomethyl, cyano, alkoxycarbonyl, aryloxycarbonyl, aralkoxycarbonyl, acylamino, aroylamino, carbamoyl, alkylcarbamoyl, dialkylcarbamoyl, arylcarbamoyl, aralkylcarbamoyl, alkylsulfonyl, alkylsulfinyl, arylsulfonyl, arylsulfinyl, aralkylsulfonyl, aralkylsulfinyl, or —$NR_aR_b$ where $R_a$ and $R_b$ are independently hydrogen, alkyl, aryl, or aralkyl. Preferred aryl group substituents are alkyl, hydroxy, alkoxy, halo and trihalomethyl.

"Aralkyl" means an alkyl group substituted by an aryl radical. Preferred aralkyl groups include benzyl, naphth-1-ylmethyl naphth-2-ylmethyl, and phenethyl.

"Substituted aralkyl" means an aralkyl group substituted on the aryl portion by one or more aryl group substituents.

"Alcohol" means an alkyl group as defined herein of from 1 to about 10 carbon atoms which is substituted with one or more hydroxyl groups. The term "lower alcohol" means an alcohol of from 1 to about 4 carbon atoms substituted by a single hydroxyl group. Representative lower alcohols include methanol, ethanol, 2-propanol,1-butanol, and the like. "Glycol" means an alkyl substituted by two or more hydroxyl groups. Representative glycols include ethylene glycol, propylene glycol, and the like.

The term "ether" means a compound of formula R-O-R' wherein R and R' are lower alkyl. R and R' may be connected through one or more methylene groups atoms or through an additional oxygen atom. Representative ethers include diethyl ether, methyl tert-butyl ether, tetrahydrofuran, dioxane, and the like.

"Polar aprotic" means solvents which do not contain hydroxy groups but have a relatively high dipole moment. Representative polar aprotic solvents include acetonitrile, N,N-dimethylformamide (DMF), dimethyl sulfoxide (DMSO), 1,1-dimethoxyethane (DME), hexamethylphosphoric triamide (HMPA), and the like.

"Alkoxide" means a base of formula M—OH wherein M is an alkali metal selected from sodium, calcium, lithium and potassium.

"Carbonate" means a base of formula $M_2CO_3$ wherein M is selected from magnesium, sodium, calcium, lithium and potassium.

"Bicarbonate" means a base of formula $MHCO_3$ wherein M is selected from sodium, calcium, lithium and potassium.

"Natural amino acid" means a carboxylic acid compound having an amino group α to the carboxylate group, i.e., is a compound of formula $H_2N$—CHR—$CO_2H$ wherein R is —H, alkyl, cycloalkyl, cycloalkylalkyl, alkylcycloalkyl, alkylcycloalkylalkyl, aryl, substituted aryl, aralkyl, substituted aralkyl, or —$CH_2CO_2Q$ wherein Q is defined herein. Preferred natural amino acids are those wherein R is cyclohexylmethyl. Preferred amino acids have L stereochemistry at the α-carbon.

"Peptide" and "polypeptide" mean a polymer in which the monomers are natural or unnatural amino acid residues joined together through amide bonds. "Peptide backbone" means the series of amide bonds through which the amino acid residues are joined.

"Amino acid residue" means the individual amino acid units incorporated into the peptides of the invention.

"Pseudopeptide" means a peptide which incorporates one or more unnatural amino acid monomers in the peptide backbone. Representative non-amino acid monomers include 1-[(phenylmethoxy)carbonyl]-4-piperidinebutanoic acid and 4-pyrdinebutyric acid.

"Unnatural amino acid" means a carboxylic acid compound having an amino group therein in a position other than α to the carboxylate group. Preferred unnatural amino acids herein include compounds of formula $NH_2(CH_2)_2CO_2H$ and

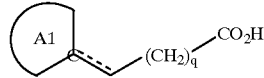

wherein

is azaheterocyclyl. Representative preferred unnatural amino acids include 4piperidinebutanoic acid, 3-(4-piperidinylmethylene)propionic acid and 4-pyridinebutyric acid.

"N-protecting group" and "nitrogen protecting group" mean an easily removable group which is known in the art to protect an amino group against undesirable reaction during synthetic procedures and to be selectively removable. The use of N-protecting groups is well known in the art for protecting groups against undesirable reactions during a synthetic procedure and many such protecting groups are known, cf., for example, T. H. Greene and P. G. M. Wuts, Protective Groups in Organic Synthesis, 2nd edition, John Wiley & Sons, New York (1991), incorporated herein by reference. Preferred N-protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrobenzyloxycarbony, 2,4-dichlorobenzyloxycarbonyl, allyoxycarbonyl (Alloc), and the like.

"Acid labile N-protecting group" and "acid labile nitrogen protecting group" mean a N-protecting group as defined above which is readily removed by treatment with acid while remaining relatively stable to other reagents. A preferred acid labile N-protecting group is tert-butoxycarbonyl (BOC).

"Hydrogenation labile N-protecting group" and "hydrogen labile nitrogen protecting group" mean an N-protecting group as defined above which is readily removed by hydrogenation while remaining relatively stable to other reagents. A preferred hydrogenation labile N-protecting group is benzyloxycarbonyl (CBZ).

"Metal-labile nitrogen protecting group" means a nitrogen protecting group as defined above which is readily removed by metals. A preferred metal-labile nitrogen protecting group is allyl, which is removed by treatment with Pd(0).

"N-protecting agent" means a reagent used to introduce a N-protecting group into the molecular entity. Such protecting groups are generally introduced by displacement of a leaving group from the N-protecting agent by the nucleophilic nitrogen atom which is to be protected. Representative N-protecting agents include acyl and aryl halides including acetyl chloride and benzoyl chloride, and the like; acyl and aryl anhydrides including acetic anhydride, trifluoroacetic anhydride and benzoic anhydride, and the like; formates including benzyl chloroformate; and carbonates such as di-tert-butyldicarbonate and benzyl-N-succinimidyl carbonate.

"Carboxylic acid protecting group" and "acid protecting group" mean an easily removable group which is known in the art to protect a carboxylic acid (—CO₂H) group against undesirable reaction during synthetic procedures and to be selectively removable. The use of carboxylic acid protecting groups is well known in the art and many such protecting groups are known, cf., for example, T. H. Greene and P. G. M. Wuts, Protective Groups in Organic Synthesis, 2nd edition, John Wiley & Sons, New York (1991), incorporated herein by reference. Examples of carboxylic acid protecting groups include esters such as methoxymethyl, methylthiomethyl, tetrahydropyranyl, benzyloxymethyl, substituted and unsubstituted phenacyl, 2,2,2-trichloroethyl, tert-butyl, cinnamyl, substituted and unsubstituted benzyl, trimethylsilyl, allyl, and the like, and amides and hydrazides including NN-dimethyl, 7-nitroindolyl, hydrazide, N-phenylhydrazide, and the like. Especially preferred carboxylic acid protecting groups are tert-butyl and benzyl.

"Hydrogenation labile carboxylic acid protecting group" and "hydrogenation labile acid protecting group" mean an acid protecting group as defined above which is readily removed by hydrogenation while remaining relatively stable to other reagents. A preferred hydrogenation labile acid protecting group is benzyl.

"Acid labile carboxylic acid protecting group" and "acid labile acid protecting group" mean an acid protecting group as defined above which is readily removed by treatment with acid while remaining relatively stable to other reagents. A preferred acid labile acid protecting group is tert-butyl.

"Metal labile carboxylic acid protecting group" and "metal labile acid protecting group" mean an acid protecting group as defined above which is readily removed by treatment with metal. Preferred metal to labile acid protecting groups are phenacyl and allyl, which are removed by treatment with Zn or Pd(0).

"Acyl activating group" means a group which, when substituted for the hydroxy group of a carboxylic acid, renders the carbonyl group more susceptible to nucleophilic attack, thereby facilitating replacement of the hydroxy group with nucleophiles. Representative acyl activating groups include halogen (i.e., acyl halides); esters of the carboxylic acid with hydroxybenzotriazole, N-hydroxysuccinimide, pentafluorophenol, p-nitrophenol, and the like; symmetric anhydrides; asymmetric anhydrides, prepared, for example, by reaction of the carboxylic acid with isopropyl chloroformate, ethyl chloroformate, isobutyl chloroformate, and the like; N-carboxy anhydrides; the products resulting from reaction of the carboxylic acid with carbodiimides such as dicyclohexyl-, diisopropyl-, and NN-dimethylpropylethylcarbodiimide; and the derivatives resulting from reaction of the carboxylic acid with (benzotriazole-1-yloxy)tris-(dimethylamino) phosphoronium hexafluorophosphate, (benzotriazole-1yloxy)tris-(pyrrolidino) phosphoronium hexafluorophosphate,
2-(1H-benzotriazol-1-yl)-1,1,3,3-tetramethyluronium tetrafluoroborate,
2-(1H-benzotriazol-1-yl)-1,1,3,3-tetramethyluronium hexafluorophosphate and diphenylphosphorazidate.

"Salt" used in conjunction with the pseudotetrapeptide, pseudodipeptide and dipeptide herein includes the acid and base addition salts.

Where the pseudotetrapeptide, pseudodipeptide and dipeptide is substituted with a basic moiety, acid addition salts are optionally formed and may be a more convenient form for use. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, trifluoroacetate, citrate, lactate, tartarate, malonate, oxalate, salicylate, propionate, succinate, fumarate, maleate, methylene-bis-β-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

According to a further feature of the invention, acid addition salts of the pseudotetrapeptide, pseudodipeptide or dipeptide are prepared by reaction of the free base with the appropriate acid, by the application or adaptation of known methods. For example, the acid addition salts of the peptides of this invention are prepared either by dissolving the free base in aqueous or aqueous-alcohol solution or other suitable aqueous solvent mixtures containing the appropriate acid and isolating the salt by evaporating the solution, or by reacting the free base and acid in an organic solvent, in which case the salt separates directly or can be obtained by concentration of the solution.

The pseudotetrapeptide, pseudodipeptide or dipeptide can be regenerated from the salts by the application or adaptation of known methods. For example, the pseudotetrapeptide, pseudodipeptide or dipeptide can be regenerated from their acid addition salts by treatment with an alkali, e.g. aqueous sodium bicarbonate solution or aqueous ammonia solution.

Where the pseudotetrapeptide, pseudodipeptide or dipeptide is substituted with an acidic moiety, base addition salts may be formed and may be a more convenient form for use. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial effects inherent in the free acid are not vitiated by side effects ascribable to the cations. Pharmaceutically acceptable salts, including for example alkali and alkaline earth metal salts or amine salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, n-methyl-glucamine, lysine, arginine, ornithine, choline, N,N'-dibenzylethylenediamine, chloroprocaine, diethanolamine, procaine, n-benzylphenethylamine, diethylamine, dicyclohexylamine, piperazine, tris(hydroxymethyl)-aminomethane, tetramethylammonium hydroxide, and the like.

Metal salts of the pseudotetrapeptide, pseudodipeptide or dipeptide may be obtained by contacting a hydride, hydroxide, carbonate or similar reactive compound of the chosen metal in an aqueous or organic solvent with the free acid form of the pseudotetrapeptide, pseudodipeptide or dipeptide. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating or cooling.

Amine salts may be obtained by contacting an amine in an aqueous or organic solvent with the free acid form of the pseudotetrapeptide, pseudodipeptide or dipeptide. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The pseudotetrapeptide, pseudodipeptide or dipeptide can be regenerated from their base addition salts by the application or adaptation of known methods, for example, by treatment of the base addition salt with an acid, e.g. hydrochloric acid.

Salts of the pseudotetrapeptide, pseudodipeptide or dipeptide are also useful for purification of the pseudotetrapeptide, pseudodipeptide or dipeptide, for example by exploitation of the solubility differences between the salts and the parent peptides, side products and/or starting materials by techniques well known to those skilled in the art.

"Pharmaceutically acceptable ester" means esters which hydrolyze in vivo and include those that break down readily in the human body to leave the parent azacycloalkylalkanoyl pseudotetrapeptide or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

"Pharmaceutically acceptable prodrug" means a peptide which is, within the scope of sound medical judgement, suitable for pharmaceutical use in a patient without undue toxicity, irritation, allergic response, and the like, and effective for the intended use, including a pharmaceutically acceptable ester as well as a zwitterionic form, where possible, of the peptides of the invention. The term "prodrug" means a peptide which is rapidly transformed in vivo to yield the parent peptide, for example by hydrolysis in blood. Pharmaceutically acceptable prodrugs according to the invention are described in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The pseudotetrapeptide, pseudodipeptide or dipeptide may contain asymmetric centers in addition to the chiral centers in the backbone of the peptide. These asymmetric centers may independently be in either the R or S configuration. It will also be apparent to those skilled in the art that certain peptides of formula I may exhibit geometrical isomerism. Geometrical isomers include the cis and trans forms of peptides of the invention having alkenyl moieties. The present invention comprises the preparation of the individual geometrical isomers and stereoisomers and mixtures thereof.

Such isomers can be separated from their mixtures by the application or adaptation of known methods, for example chromatographic techniques and recrystallization techniques, or they are separately prepared from the appropriate isomers of their intermediates, for example by the application or adaptation of methods described herein.

Preferred Embodiments

Preferred pseudotetrapeptides for preparation using the process of this invention are those of formula II

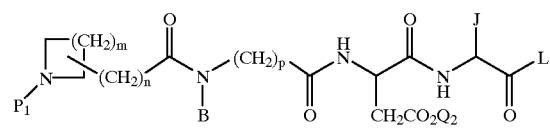

wherein $P_1$ is a nitrogen protecting group; B is alkyl, cycloalkyl, cycloalkylalkyl, alkylcycloalkyl, alkylcycloalkylalkyl; $Q_2$ is H or a carboxylic acid protecting group $P_2$; J is —H, alkyl, cycloalkyl, cycloalkylalkyl, alkylcycloalkyl, or alkylcycloalkylalkyl; L is $OR^1$ or $NR^1R^2$, where $R^1$ and $R^2$ are independently —H, alkyl, cycloalkyl, cycloalkylalkyl, alkylcycloalkyl, alkylcycloalkylalkyl, aryl, aralkyl, alkylaryl, or alkylaralkyl; m is 3; and n is 3 or 4.

More preferred pseudotetrapeptides for preparation using the process of this invention are those of formula II wherein B is alkyl; J is alkyl, cycloalkyl, or cycloalkylalkyl; L is $OR^1$ or $NR^1R^2$, where $R^1$ and $R^2$ are independently —H, alkyl, cycloalkyl, cycloalkylalkyl, alkylcycloalkyl, or alkylcycloalkylalkyl; m is 3; n is 3 or 4; and p is 1.

Still more preferred pseudotetrapeptides for preparation using the process of this invention are those of formula III

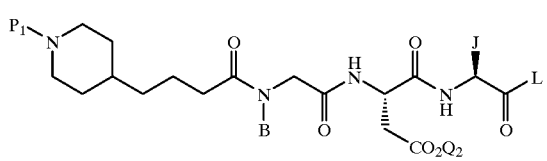

III wherein $P_1$ is a nitrogen protecting group; B is alkyl; $Q_2$ is H or a carboxylic acid protecting group $P_2$; J is alkyl, cycloalkyl, or cycloalkylalkyl; and L is $OR^1$ or $NR^1R^2$, where $R^1$ and $R^2$ are independently —H, alkyl, cycloalkyl, cycloalkylalkyl, alkylcycloalkyl, or alkylcycloalkylalkyl.

The most preferred compounds for preparation according to this invention are those of formula III wherein B is alkyl; J is cycloalkylalkyl; and L is $NR^1R^2$ wherein $R^1$ and $R^2$ are independently H or alkyl.

In another aspect, this invention is directed to a process wherein $Q_2$ is a carboxylic acid protecting group.

In another aspect, this invention is directed to a process wherein $P_1$ is benzyloxycarbonyl and $Q_2$ is benzyl.

In another aspect, this invention is directed to a process wherein $P_1$ is benzyloxycarbonyl and $Q_2$ is H.

In another aspect, this invention is directed to a process wherein $P_1$ is benzyloxycarbonyl, $Q_2$ is benzyl and L is $—NR^1R^2$.

In another aspect, this invention is directed to a process wherein $P_1$ is benzyloxycarbonyl, $Q_2$ is H and L is $—NR^1R^2$.

In another aspect, this invention is directed to a process wherein the salt of the azaheterocyclyl pseudodipeptide is coupled with the salt of the carboxylic acid substituted dipeptide.

In another aspect, this invention is directed to a process wherein a base addition salt of the azaheterocyclyl pseudodipeptide is coupled with an acid addition salt of the carboxylic acid dipeptide.

In another aspect, this invention is directed to a process wherein the dicyclohexylamine salt of the azaheterocyclyl pseudodipeptide is coupled with the trifluoroacetate salt of the carboxylic acid dipeptide.

In another aspect, this invention is directed to a process comprising (a) coupling a azaheterocyclyl pseudodipeptide of formula

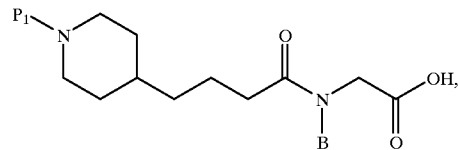

or a base addition salt thereof, wherein $p_1$ is a nitrogen protecting group and B is alkyl, with a carboxylic acid substituted dipeptide of formula

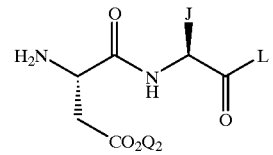

or an acid addition salt thereof wherein $Q_2$ is H or a carboxylic acid protecting group; J is alkyl, cycloalkyl, or cycloalkylalkyl; and L is $OR^1$ or $NR^1R^2$, where $R^1$ and $R^2$ are independently H, alkyl, cycloalkyl, cycloalkylalkyl, alkylcycloalkyl, alkylcycloalkylalkyl or aralkyl, to prepare a pseudotetrapeptide of formula

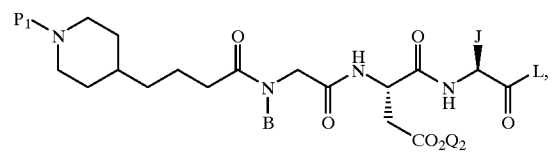

(b) optionally removing the nitrogen protecting group or carboxylic acid protecting group and
(c) optionally converting the pseudotetrapeptide its salt of prodrug.

In another aspect of the above process, $P_1$ is benzyloxycarbonyl and $Q_2$ is a benzyl.

In another aspect of the above process, $P_1$ is benzyloxycarbonyl and $Q_2$ is H.

In another aspect of the above process, $P_1$ is benzyloxycarbonyl; $Q_2$ is a benzyl; B is ethyl; J is cyclohexylmethyl; and L is $NH_2$.

In another aspect of the above process, $P_1$ is benzyloxycarbonyl; $Q_2$ is H; B is ethyl; J is cyclohexylmethyl; and L is $NH_2$.

In another aspect, this invention is directed to a process for preparing a cyclohexylmethyl substituted dipeptide of formula

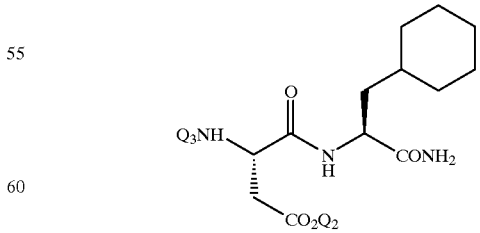

a wherein $Q_2$ is H or a carboxylic acid protecting group and $Q_3$ is H or a nitrogen protecting group, comprising
(a) reducing a phenylmethyl substituted peptide of formula

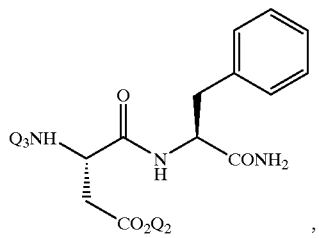

, and (b) optionally removing the nitrogen protecting group or carboxylic acid protecting group.

In another aspect of the above process, the reducing is carried out by catalytic hydrogenation.

In another aspect of the above process, the catalytic hydrogenation is carried out using a platinum catalyst.

In another aspect of the above process, the platinum catalyst is platinum oxide or platinum on alumina.

In another aspect, this invention is directed to a process for preparing an amido dipeptide of formula

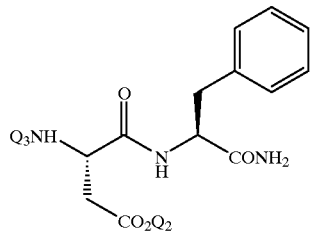

wherein $Q_2$ is H or a base addition salt, or a carboxylic acid protecting group and $Q_3$ is H or a nitrogen protecting group comprising amidating a peptide ester of formula

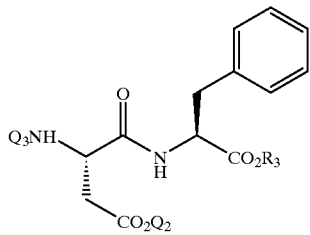

wherein $R_3$ is lower alkyl.

In another aspect of the above process, the amidating is carried out using ammonia in alcohol.

In another aspect of the above process, the alcohol is a lower alcohol.

In another aspect of the above process, the amidating is carried out using ammonia in a lower alcohol-glycol solvent mixture.

In another aspect of the above process, the lower alcohol-glycol solvent mixture comprises methanol and ethylene glycol.

In another aspect, this invention is directed to a process for preparing a protected aspartame compound of formula

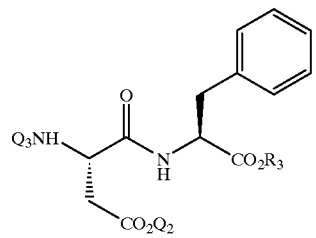

wherein $Q_2$ is H or a carboxylic acid protecting group; $Q_3$ is a nitrogen protecting group; and $R_3$ is lower alkyl; comprising introducing a N-protecting group to an aspartame compound of formula

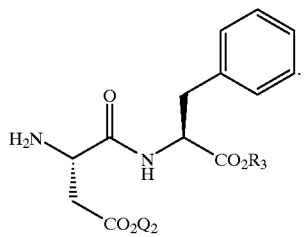

In another aspect of the above process, $Q_3$ is benzyloxycarbonyl or 1-butyloxycarbonyl.

In another aspect of the above process, $Q_2$ is H.

In another aspect, this invention is directed to a process for preparing an amido dipeptide of formula

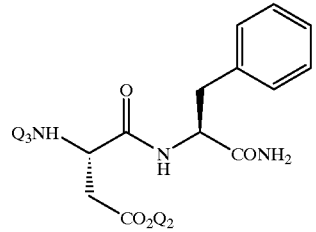

wherein $Q_3$ is a nitrogen protecting group and $Q_2$ is H, comprising
  (a) adding base and a N-protecting agent to a solution of aspartame in a solvent to form a solution of a compound of formula

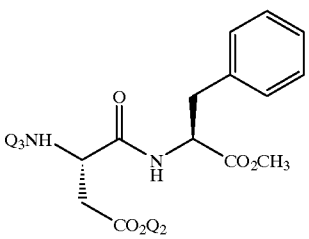

wherein $Q_2$ is H or a base addition salt, and
  (b) introducing ammonia into the resultant solution of step (a).

In another aspect of the above process, $Q_3$ is tert-butyloxycarbonyl or benzyloxycarbonyl.

In another aspect of the above process, $Q_3$ is tert-butyloxycarbonyl.

In another aspect of the above process, the solvent is alcohol.

In another aspect of the above process, the alcohol is a lower alcohol or a lower alcohol-glycol mixture.

In another aspect of the above process, the alcohol is methanol or a methanol-ethylene glycol mixture.

In another aspect, this invention is directed to a process for preparing a cyclohexylmethyl substituted dipeptide of formula

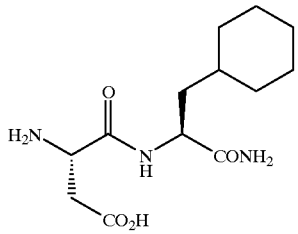

or an acid addition salt thereof, comprising (a) preparing a mixture of a catalyst and a phenylmethyl substituted peptide of formula

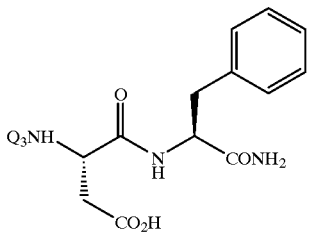

wherein $Q_3$ is tert-butyloxycarbonyl in a solvent, (b) treating the mixture with hydrogen, (c) removing the catalyst from the mixture, and (c) introducing gaseous HCl into the mixture.

In another aspect of the above process, the solvent is acetic acid.

In another aspect, this invention is directed to a process for preparing an azaheterocyclyl substituted acid compound of formula

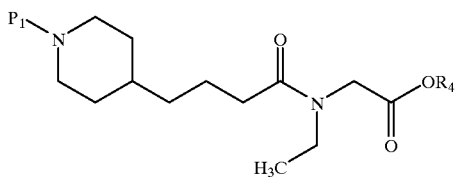

wherein $R_4$ is H or lower alkyl and $P_1$ is a nitrogen protecting group, comprising (a) decarboxylating a 2-pyridylethyl-di-(lower alkyl) malonate of formula

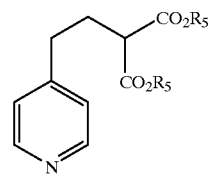

wherein $R_5$ is lower alkyl to prepare a pyridyl acid of formula;

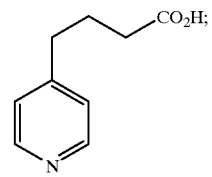

(b) hydrogenating the pyridyl acid with hydrogen in the presence of a catalyst to prepare a piperidine acid of formula

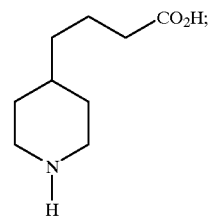

(c) optionally removing the catalyst;

(d) N-protecting the piperidine acid to prepare a nitrogen-protected piperidine acid of formula

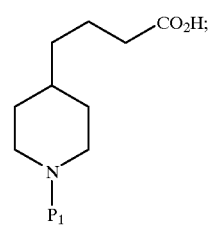

(e) coupling the nitrogen-protected piperidine acid with a N-ethylglycine compound of formula

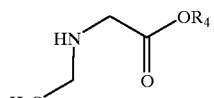

to prepare the azaheterocyclyl substituted acid compound; and (f) optionally deesterifying the azaheterocyclyl substituted compound wherein $R_4$ is lower alkyl.

In another aspect of the above process, $P_1$ is benzyloxycarbonyl and $R_4$ is H.

In another aspect of the above process, the decarboxylating is carried out by heating the 2-pyridylethyl-di-(lower alkyl)malonate in an aqueous acid solution.

In another aspect of the above process, the aqueous acid is aqueous HCl.

In another aspect of the above process, the hydrogenating is carried out in an aqueous acid solution.

In another aspect of the above process, the aqueous acid is aqueous HCl.

In another aspect of the above process, N-protecting is carried out in an aqueous base solution.

In another aspect of the above process, $P_1$ is benzyloxycarbonyl.

In another aspect of the above process:

(a) a solution in aqueous acid of the 2-pyridylethyl-di-(lower alkyl) malonate is heated to prepare a solution of the pyridyl acid in aqueous acid;

(b) a catalyst is added to the solution of pyridyl acid and the mixture is treated with hydrogen to form a mixture of catalyst and the piperidine acid;

(c) the catalyst is separated the from the mixture to prepare an aqueous solution of piperidine acid; and (d) base and a N-protecting agent are added to the aqueous solution to prepare the N-protected piperidine acid.

In another aspect of the above process, the aqueous acid is aqueous HCl.

In another aspect of the above process, $R_4$ is H.

In another aspect of the above process, $P_1$ is benzyloxycarbonyl.

In another aspect, this invention is directed to a process for preparing a pseudotetrapeptide of formula

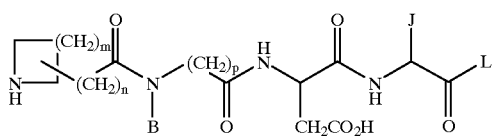

or a salt or prodrug thereof, wherein m is 3; n is 2–6; B is alkyl; p is 1 or 2; J is cyclohexylmethyl; and L is $OR_1$ or $NR_1R_2$ wherein $R_1$ and $R_2$ are independently —H, alkyl, cycloalkyl, cycloalkylalkyl, alkylcycloalkyl, alkylcycloalkylalkyl, comprising (a) reducing a compound of formula

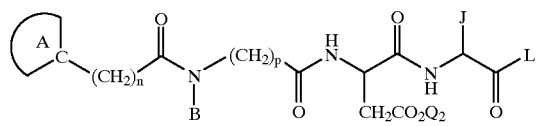

wherein

is pyridyl or

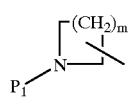

wherein m is 3 and $P_1$ is H or a nitrogen protecting group; $Q_2$ is H or a carboxylic acid protecting group; and J is phenylmethyl;

(b) optionally removing the nitrogen protecting group or carboxylic acid protecting group; and (c) optionally converting the pseudotetrapeptide to the salt or prodrug.

In another aspect of the above process, reducing is by catalytic hydrogenation.

In another aspect of the above process,

is

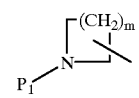

wherein m is 3 and $P_1$ is a nitrogen protecting group; n is 3; p is 1; and $Q_2$ is a carboxylic acid protecting group.

In another aspect of the above process, $P_1$ is a hydrogenation labile nitrogen protecting group; and $Q_2$ is a hydrogenation labile carboxylic acid protecting group.

In another aspect of the above process, the catalytic reduction effects simultaneous reduction and removal of $P_1$ and $Q_2$.

In another aspect of the above process,

is pyridyl and $Q_2$ is a carboxylic acid protecting group.

In another aspect of the above process, $Q_2$ is a hydrogenation labile carboxylic acid protecting group.

In another aspect of the above process, the catalytic reduction effects simultaneous reduction and removal of $Q_2$.

In another aspect, this invention is directed to a pseudotetrapeptide of formula

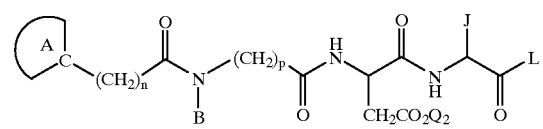

or a salt or prodrug thereof wherein

is pyridyl or

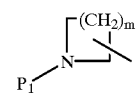

wherein m is 3; $P_1$ is H or a nitrogen protecting group; n is 2–6; B is alkyl; p is1 or 2; $Q_2$ is H or a carboxylic acid protecting group; J is phenylmethyl; and L is $OR_1$ or $NR_1R_2$ wherein $R_1$ and $R_2$ are independently —H, alkyl, cycloalkyl, cycloalkylalkyl, alkylcycloalkyl, alkylcycloalkylalkyl.

In another aspect, this invention is directed to the psuedotetrapeptide defined above wherein is

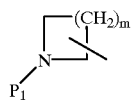

wherein m is 3; $P_1$ is a nitrogen protecting group; n is 3; p is 1; and $Q_2$ is a carboxylic acid protecting group.

In another aspect, this invention is directed to the psuedotetrapeptide defined above wherein $P_1$ is a hydrogenation labile nitrogen protecting group and $Q_2$ is a hydrogenation labile carboxylic acid protecting group.

In another aspect, this invention is directed to a pseudodipeptide of formula

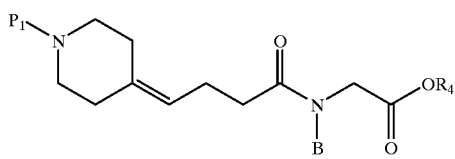

or a salt thereof wherein $P_1$ is H or a nitrogen protecting group; B is alkyl, cycloalkyl, cycloalkylalkyl, alkylcycloalkyl, alkylcycloalkylalkyl, aryl, aralkyl, alkylaryl or alkylaralkyl; and $R_4$ is H or lower alkyl.

In another aspect, this invention is directed to the psuedodipeptide defined above wherein $P_1$ is a nitrogen protecting group, B is alkyl and $R_4$ is H. In another aspect, this invention is directed to the psuedodipeptide defined above $P_1$ is benzyloxycarbonyl and B is ethyl.

The present invention is illustrated by the following schemes and demonstrative examples, which are presented for purposes of illustration and are not intended to limit the scope of the invention.

As used below, the following abbreviations shall be understood to have the following meanings: BOC (t-butyloxycarbonyl), CBZ or Z (benzyloxycarbonyl), Gly (glycine), Asp (aspartic acid), Obzl (benzyloxy), TFA (trifluoroacetic acid), Cha (β-cyclohexylalanine), EtOAc (ethyl acetate), DMF (dimethyl formamide), DCC (dicyclohexylcarbodiimide), HOBT (hydroxybenzotriazole), TBTU (2-1H-Benzotriazol-1-yl)-1, 1,3,3-tetramethyluronium tetrafluoroborate), DI (deionized water), PNP (p-nitrophenol), PFP (pentafluorophenol), DCU (dicyclohexyl urea), NMM (N-methylmorpholine) and MTBE (methyl tert-butyl ether).

As shown in Scheme 1, this invention comprises the coupling of a azaheterocyclyl pseudodipeptide of formula IV with a carboxylic acid substituted dipeptide of formula V to form the pseudotetrapeptide of formula I. It is understood that in Scheme 1, B, J, K, L, m, p, q and $Q_2$ are as defined above.

During the preparation of azaheterocyclyl pseudotetrapeptides of formula I or intermediates thereto, it may also be desirable or necessary to prevent cross-reaction between chemically active substituents present on the naturally occurring or pseudo amino acids or peptides. The substituents may be protected by standard protecting groups which may subsequently be removed or retained, as required, by known methods to afford the desired products or intermediates (see, for example, Green, "Protective Groups in Organic Synthesis", Wiley, New York, 1981). Selective protection or deprotection may also be necessary or desirable to allow conversion or removal of existing substituents, or to allow subsequent reaction to afford the final desired product.

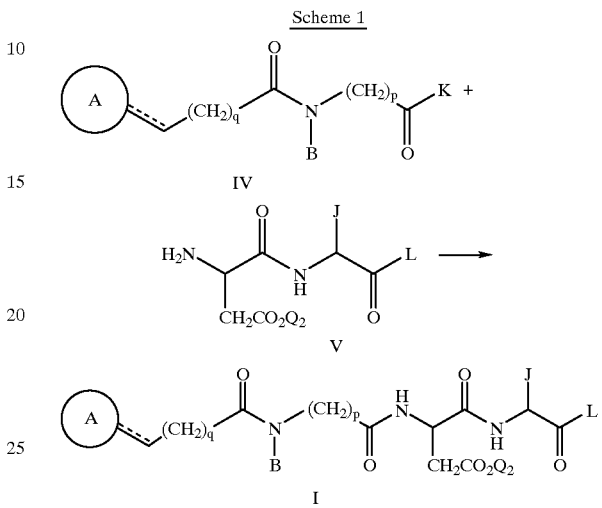

The coupling of the azaheterocyclyl pseudodipeptide of formula IV with a carboxylic acid substituted amdipeptide of formula V described above is accomplished in the presence of an organic base such as N-methylmorpholine, diisopropylethylamine or triethylamine. Suitable solvents for the coupling reaction include dichloromethane, toluene, N,N-dimethylformamide, ethyl acetate, acetonitrile, dimethyl acetamide, N-methylpyrrolidone and water, and mixtures thereof. Coupling times range from about 30 minutes to about 24 hours, depending upon the dipeptide and pseudodipeptide to be coupled, activating agent, solvent and temperature. The coupling is accomplished at a temperature of from about −10° C. to about 50° C., preferably at about ambient temperature. The carboxylic acid moiety of IV is preferably activated with an appropriate activating agent. Representative activating agents include isopropyl chloroformate in the presence of N-methylpiperidine, 1-(3-dimethylaminopropyl)-3-ethylcarbodiimide hydrochloride (EDC) in the presence of 1-hydroxybenzotriazole (HOBT), bis(2-oxo-3-oxazolidinyl)-phosphonic chloride (BOP-Cl) in the presence of triethylamine, 2-(1H-benzotriazole-1-yl)-1.1.3.3-tetramethyluronium tetrafluoroborate (TBTU) in the presence of diisopropylethyl amine, N-hydroxysuccinimide in the presence of N,N'-dicyclohexylcarbodiimide (DCC), and the like. This activation is preferably accomplished at a temperature of from about 0° C. to about 10° C. over about 5 minutes to about 5 hours.

In cases wherein the acyl-activated moiety is stable, it may be prepared and isolated in advance for use in the coupling reaction. Acyl activating groups suitable for the preparation of isolable pseudodipeptides of formula IV wherein K is an acyl activating group include, the esters with hydroxybenzotriazole, N-hydroxysuccinimide, pentafluorophenol, p-nitrophenol, symmetric anhydrides, acyl halides, and the like.

In the coupling reaction described above wherein K is OH, the azaheterocyclyl pseudodipeptide of formula IV may be utilized as the free carboxylic acid or as the base addition salt of the carboxylic acid. Preferred base addition salts include the salts with amines such as dicyclohexylamine and triethylamine, and the salts with metals such as sodium and potassium. The base addition salt with dicyclohexylamine is especially preferred. When the base addition salt is utilized, the free acid is liberated in situ prior to coupling by reaction with a suitable acid.

$Q_2$ is H, an acid labile carboxylic acid protecting group such as tert-butyl, a base labile carboxylic acid protecting group such as methyl or ethyl, a hydrogenation labile carboxylic acid protecting group such as benzyl or a carboxylic acid protecting group which is readily cleaved by metals such as Zn or Pd(0), for example phenacyl.

Scheme 2

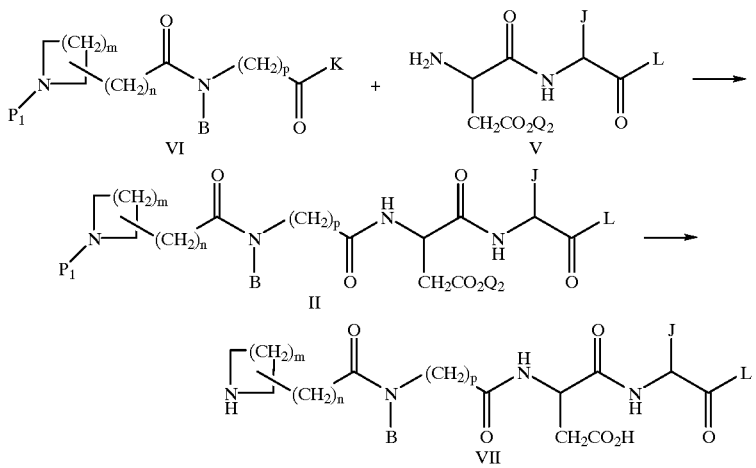

Likewise, the dipeptide V may be utilized as the free base, the acid addition salt, or the base addition salt. Acid addition salts are preferred. Suitable acid addition salts include hydrochloride, hydrobromide, trifluoroacetate, acetate and tosylate. Especially preferred acid addition salts include hydrochloride and trifluoroacetate.

The use of acid and base addition salts is especially advantageous as it allows for the purification of the building block azaheterocyclyl pseudodipeptides and carboxylic acid substituted dipeptides IV and V by acid-base extraction techniques as well as by recrystallization of the salt, thereby eliminating the need for purification by, for example, chromatography, and allows the use of intermediates as aqueous solutions, thereby rendering isolation of the discrete intermediates unnecessary.

In an especially preferred aspect of the coupling reaction, $Q_2$ is H. The unexpected discovery that coupling proceeds cleanly without protection of the side-chain carboxylic acid moiety confers several advantages to the process. The total number of steps is reduced as protection and deprotection reactions are eliminated, and furthermore, the unprotected acid allows isolation and purification of the dipeptide V and the coupling product I by acid-base extraction techniques or recrystallization of the base addition salt as described above.

The pseudotetrapeptide of formula I in which the ring A is unsaturated may be converted to the saturated derivative by selective reduction of the ring double bonds, for example by catalytic hydrogenation using platinum oxide. Any nitrogen protecting groups $P_1$ and carboxylic acid protecting groups $P_2$ present in the pseudotetrapeptide I may also be removed as described below.

Compounds of formula II are preferably prepared as shown in Scheme 2. In Scheme 2, m, n, B, K, J and L have the values defined above; $P_1$ is an acid labile N-protecting group such as tert-butyloxycarbonyl or a hydrogenation labile N-protecting group such as benzyloxycarbonyl; and According to the foregoing Scheme 2. the pseudodipeptide VI is coupled with the dipeptide V as described in Scheme 1 above. The coupled product II is purified by recrystallization from an organic solvent or mixture of organic solvents, preferably ethyl acetate-heptane, or by precipitation of the base addition salt. The preferred base addition salt is the dicyclohexylamine salt. Salt formation is typically performed at a temperature of from about ambient temperature to about 75° C. Suitable solvents for salt formation include alcohols, ethers, esters and polar aprotic solvents, with or without admixture with water. A preferred solvent system for salt formation is acetonitrile-water.

After coupling of VI and V to prepare II, the nitrogen protecting group $P_1$ and, if present, the carboxylic acid protecting group $P_2$ are removed sequentially or in a single operation to produce the tetrapeptide or pseudopeptide VII. Acid-labile protecting groups are preferably removed with trifluoroacetic acid. Hydrogenation-labile protecting groups are preferably removed by hydrogenation over palladium on carbon. Metal labile protecting groups are removed by treatment with Zn or Pd(0). Solvents for the hydrogenation reaction are preferably lower alcohols such as methanol, ethanol or propanol, or alcohol-water mixtures such as ethanol-water or propanol-water. The pseudotetrapeptide VII is purified by recrystallization from lower alcohols or lower alcohol-water mixtures, preferably from methanol or ethanol or mixtures of methanol and water or ethanol and water.

The preparation of pseudotetrapeptides of formula III in accordance with the process of this invention is outlined in Scheme 3. In Scheme 3, $P_1$ is a hydrogenation-labile N-protecting group; $Q_2$ is H or a hydrogenation-labile carboxylic acid protecting group; B is alkyl; J is alkyl, cycloalkyl, or cycloalkylalkyl; and L is $OR^1$ or $NR^1R^2$, where $R^1$ and $R^2$ are independently —H, alkyl, cycloalkyl, cycloalkylalkyl, alkylcycloalkyl, or alkylcycloalkylalkyl.

Scheme 3

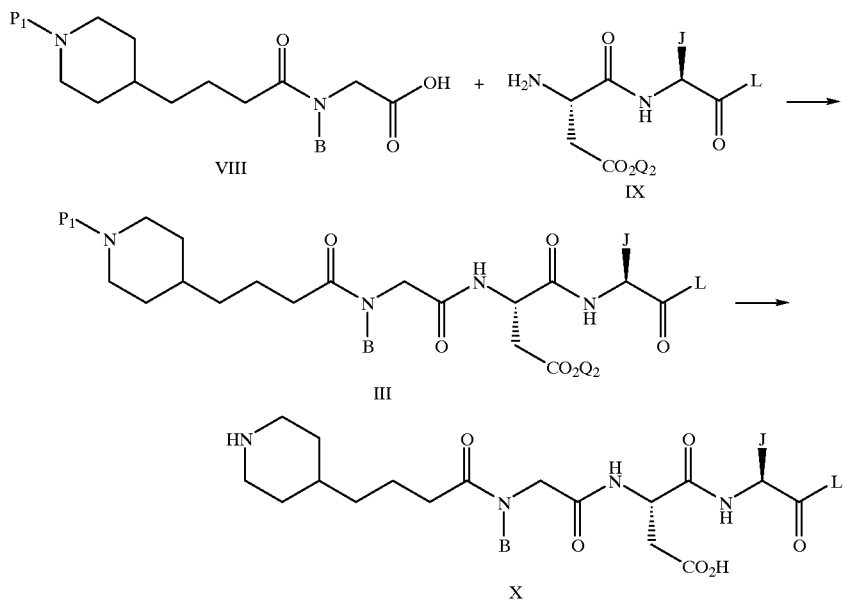

According to the foregoing Scheme 3, pseudodipeptide VIII is activated and coupled with the dipeptide IX as described in Scheme 1 above. Preferred activating agents include 2-(1H-benzotriazole-1-yl)-1,1,3,3-tetramethyluronium tetrafluoroborate (TBTU) in the presence of diisopropylethyl amine and N-hydroxysuccinimide in the presence of N,N'-dicyclohexylcarbodiimide (DCC). Activation is preferably accomplished at a temperature of from about 0° C. to about 10° C. over about 5 minutes to about 5 hours.

In the coupling reaction described in Scheme 3 above, the pseudodipeptide VIII is preferably utilized as the base addition salt. Preferred base addition salts include the salts with amines such as dicyclohexylamine and triethylamine, and the salts with metals such as sodium and potassium. The base addition salt with dicyclohexylamine is especially preferred.

The dipeptide IX is preferably utilized as the acid addition salt. Suitable acid addition salts include hydrochloride, hydrobromide, trifluoroacetate, acetate and tosylate. Especially preferred acid addition salts are hydrochloride and trifluoroacetate.

The coupled product III is purified by recrystallization from an organic solvent or mixture of organic solvents, preferably ethyl acetate-heptane, or by precipitation of the base addition salt. The preferred base addition salt is the dicyclohexylamine salt. Salt formation is typically performed at a temperature of from about ambient temperature to about 75° C. Suitable solvents for salt formation include alcohols, ethers, esters and polar aprotic solvents with or without admixture with water. A preferred solvent system for salt formation is acetonitrile-water.

In an especially preferred aspect of the coupling reaction of Scheme 3, $Q_2$ is H.

After coupling of pseudodipeptide VIII and dipeptide IX to prepare product III, the hydrogenation-labile protecting groups $P_1$ and $Q_2$ are removed in a single operation by hydrogenation over palladium on carbon. Solvents for the hydrogenation reaction are preferably alcohols such as methanol or ethanol, or alcohol-water mixtures such as ethanol-water. The tetrapeptide or pseudopeptide X is purified by recrystallization from a lower alcohol or a lower alcohol-water mixture, preferably from methanol or ethanol or a methanol-water or ethanol-water mixture.

The preparation of the representative pseudodipeptide VIII, wherein $P_1$ is benzyloxycarbonyl and B is ethyl is outlined in Scheme 4. It is understood that the synthetic methodology described in scheme 4 is readily extended to pseudodipeptides of formula VIII wherein $P_1$ and B are other than benzyloxycarbonyl and ethyl, respectively.

Scheme 4

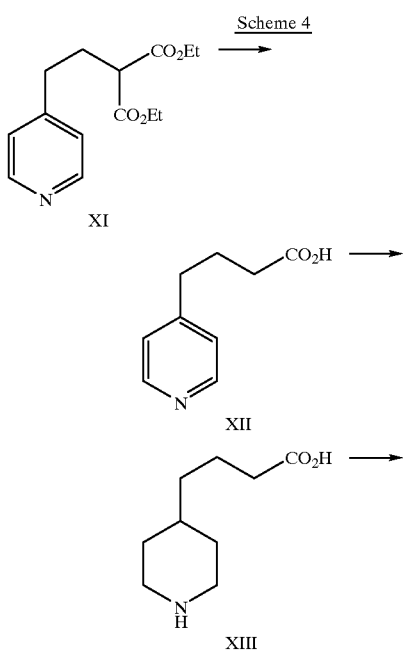

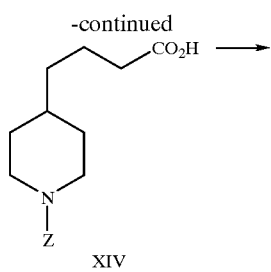

XIV

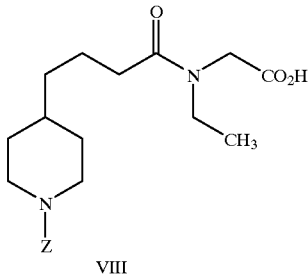

VIII

Z = benzyloxycarbonyl

According to the foregoing Scheme 4, 2-(4-pyridyl) ethylmalonic acid diethyl ester (XI, prepared, for example, by condensation of diethyl malonate with 4-vinylpyridine) is decarboxylated by heating in aqueous acid to give 4-(4-pyridyl)butanoic acid XII. The pyridine ring is then reduced by catalytic hydrogenation to give 4-(piperidin-4-yl) butanoic acid XIII. Platinum catalysts such as platinum on carbon, platinum(IV) oxide and platinum on alumina are preferred. Platinum on alumina is particularly preferred as the catalyst can be readily regenerated. The hydrogenation is carried out in alcohol, aqueous alcohol or water under a hydrogen pressure of from about atmospheric pressure to about 5 bars of hydrogen at a temperature of from ambient temperature to about 70° C. Lower temperatures can be used if the pressure of hydrogen is increased. The piperidyl N atom is then protected, for example by reaction of XIII with aqueous base and benzyl chloroformate or benzyl-N-succinimidyl carbonate to form XIV. Coupling of XIV with N-ethylglycine or N-ethylglycine ethyl ester followed by saponification of the ester with aqueous alkoxide provides VIII. The coupling is preferably accomplished by activating the carboxylic acid moiety of XIV by conversion to the acid chloride, followed by addition of N-ethylglycine or N-ethylglycine ethyl ester in the presence of base. The acid addition salts, preferably trifluoroacetate, of N-ethylglycine or N-ethylglycine ethyl ester may also be utilized. Suitable bases include amines such as diisopropylethylamine or aqueous alkoxide.

In an especially preferred preparation of VIII, 2-(4-pyridyl)ethylmalonic acid diethyl ester is taken up in aqueous acid, preferably aqueous HCl, and decarboxylated by heating at reflux. A catalyst as described above is then added to the resulting solution of 4-(4-pyridyl)butanoic acid XIII and the mixture is catalytically hydrogenated to give an aqueous solution of 4-(4-piperidyl)butanoic acid XIV. The catalyst is then filtered off, the acidic solution of XIV is made basic with aqueous alkoxide and the benzyloxycarbonyl protecting group is introduced as described above. The 1-[(phenylmethoxy)carbonyl]-4-piperidinebutanoic acid is then extracted into an organic solvent and condensed with N-ethylglycine as described above to give VIII.

The foregoing process is especially useful as it avoids isolation of intermediates and only involves a single purification step. The various intermediates are carried forward as aqueous or organic solutions, thereby reducing costs and increasing production efficiency.

The preparation of the dipeptide of formula IX wherein $Q_2$ is H, J is cyclohexylmethyl and L is $NH_2$ is outlined in Scheme 5. Key features of the process described in Scheme 5 include the heretofore undisclosed protection of aspartame with an acid labile or hydrogenation labile protecting group $Q_3$, followed by a mild amidation with ammonia which proceeds with retention of stereochemistry. An unexpected acceleration of the amidation reaction occurs when the reaction is run in a methanol-ethylene glycol solvent mixture.

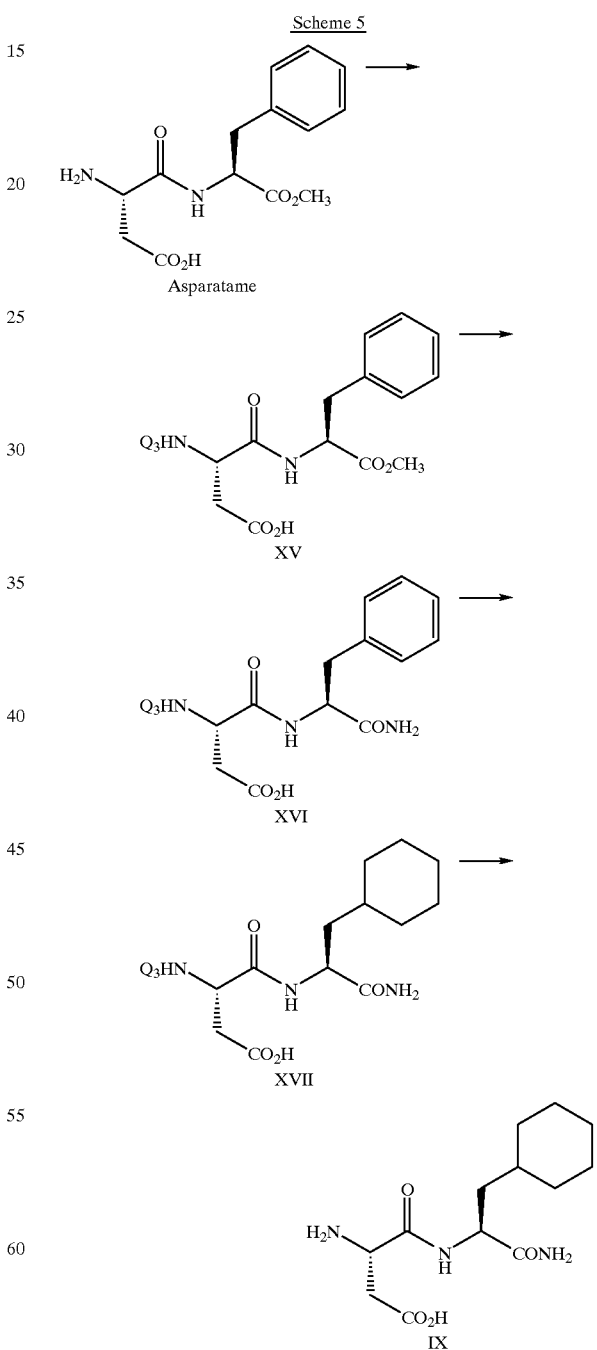

According to the foregoing Scheme 5, aspartame is protected with an acid labile N-protecting group, preferably tert-butyloxycarbonyl, or a hydrogenation labile protecting group, preferably benzyloxycarbonyl. The tert-butyloxycarbonyl protecting group is introduced by reaction of aspartame with di-tert-butyldicarbonate in the presence of an amine, preferably triethylamine, alkoxide, preferably lithium hydroxide, or carbonate. The protection is preferably run at a temperature of from about ambient temperature to about 50° C. in a lower alcohol solvent such as methanol or a lower alcohol-glycol solvent mixture such as methanol-ethylene glycol.

The protected aspartame is then amidated by treatment of a solution of the protected aspartame with ammonia gas in alcohol to give XVI. Alcohols suitable for the amidation include lower alcohols, glycols, or mixtures thereof. Preferred alcohols are methanol, ethylene glycol and methanol-ethylene glycol mixtures. The amidation is performed at a temperature of from ambient temperature to about 65° C. over from about 6 hours to about 2 days. The protected aspartame may be isolated and purified prior to amidation, or preferably, amidated by introduction of ammonia gas into the reaction mixture of the protection step.

The benzene ring of XVI is then reduced by catalytic hydrogenation to give XVII. Platinum catalysts such as platinum(IV) oxide and platinum on alumina are preferred. Platinum on alumina is particularly preferred as the catalyst can be readily regenerated. The hydrogenation is carried out in a lower alcohol, preferably butanol, or a $C_1$–$C_{10}$ saturated organic acid, preferably acetic acid. The hydrogenation is accomplished under a hydrogen pressure of from about 2 to about 5 bars of hydrogen at a temperature of from about 40° C. to about 80° C. Lower temperatures can be used if the pressure of hydrogen is increased.

When $Q_3$ is a hydrogenation labile protecting group, deprotection to provide IX is accomplished simultaneously with the reduction of the benzene ring described above. When $Q_3$ is an acid labile protecting group such as tert-butyloxycarbonyl, deprotection is preferably accomplished by treating a solution of XVII with gaseous HCl. In an especially preferred aspect, the acid labile protecting group is removed by introduction of gaseous HCl into the reaction mixture of the hydrogenation step.

One skilled in the art will readily appreciate that the present invention is well adapted to carry out the objects of the invention and obtain the ends and advantages mentioned, as well as those inherent therein. The compounds, compositions and methods described herein are presented as representative of the preferred embodiments, or intended to be exemplary and not intended as limitations on the scope of the present invention.

EXAMPLE 1

Preparation of N-[N-ethyl-N-[1-oxo-4-(4-piperidinyl)butyl]glycyl]-(L)-α-aspartyl-3-cyclohexyl-(L)-alanineamide Method A Step 1: N-[N-ethyl-N-[1-oxo-4-[1-[(phenylmethoxy)carbonyl]-4-piperidinyl]butyl]glycyl]-(L)-α-aspartyl-3-cyclohexyl-(L)-alanineamide phenylmethyl ester To a magnetically stirred 0–5° C. solution of 25.9 g (66.4 mmole) of N-ethyl-N-[1-oxo-4-[1-[(phenylmethoxy)carbonyl]-4-piperidinyl]butyl]glycine in 70 mL dimethyl formamide is added 20.9 g (65 mmole)2-(1H-benzotriazole-1-yl)-1.1.3.3-tetramethyluronium tetrafluoroborate, followed by dropwise addition of 17.6 g (130 mmole) of diisopropylethylamine. The resulting homogeneous solution is poured into a stirred, mixture of 31.8 g (65 mmole) of (L)-α-aspartyl-3-cyclohexyl-(L-alanineamide phenylmethyl ester trifluoroacetate in 30 mL of dimethylformamide at 0–5° C. Diisopropylethyl amine is added to obtain a neutral to slightly basic pH. The resulting mixture is removed from the cold bath and stirred at 23° C. overnight. The mixture is diluted with water and extracted with 4 portions of ethyl acetate. The combined ethyl acetate extracts are washed with 0.5N aqueous citric acid (3×), brine, saturated aqueous sodium bicarbonate (3×) and brine (2×), dried over magnesium sulfate, filtered, and concentrated in vacuo to give an oil which solidifies on standing to a light tan solid (50.97 g, 90.9% pure). A 36 g portion of the solid is recrystallized from ethyl acetate/heptane, to give the title compound (24 g, 95% analytically pure). MS (FAB) m/z 748, (M+Na)$^+$, 771.

Step 2: N-[N-ethyl-N-[1-oxo-4-(4-piperidinyl)butyl]glycyl]-(L)-α-aspartyl-3-cyclohexyl-(L)-alanineamide N-[N-ethyl-N-[1-oxo-4-[1[(phenylmethoxy)carbonyl]-4-piperidinyl]butyl]glycyl-(L)-α-aspartyl-3cyclohexyl-(L)-alanineamide phenylmethyl ester, prepared as in step 1 is dissolved in methanol and 10% palladium/carbon is added. The mixture is shaken under hydrogen at 50 psi for about 18 hours. The mixture is filtered through a Celite pad and the filtrate is evaporated in vacuo to give N-[N-ethyl-N-[1-oxo-4-(4-piperidinyl)butyl]glycyl-(L)-α-aspartyl-3-cyclohexyl-(L)-alanineamide. MS (FAB) m/z 524 (M+H)$^+$. NMR (300 MHz, $D_2O$)δ8.4 (1H, d), 8.1 (1H, d), 4.2 (2H, q), 4.1 (1H, s), 3.9 (4H,q), 3.4 (2H,q), 3.3 (4H, d), 2.8–3.0 (6H, m), 2.4, (2H, t), 2.2 (1H, m), 1.8 (4H, d), 1.4–1.7 (7H, m), 0.7–1.3 (10H,m).

Method B

Step 1: N-[N-ethyl-N-[1-oxo-4-[1-[(phenylmethoxy)carbonyl]-4-piperidinyl]butyl]glycyl]-(L)-α-aspartyl-3-cyclohexyl-(L)-alanineamide To a suspension of N-ethyl-N-[1-oxo-4-[1-[(phenylmethoxy)carbonyl]-4-piperidinyl]butyl]glycine dicyclohexylamine (112.5 kg) in toluene (550 kg) and water (570 kg), is added aqueous sulfuric acid (210 kg) at about 30° C. in a 2300 liter glass lined reactor. After decantation, the toluene solution is washed with a solution of aqueous sulfuric acid (210 kg) and water (390 kg). The mixture is decanted and the organic phase is washed with water (390 kg) and dried by distillation until the residual water content is below 0.5%. Acetonitrile (220 kg) and N-hydroxysuccinimide (27 kg) are added to the toluene solution. The resulting suspension is cooled to about 5° C. under nitrogen and a solution of dicyclohexylcarbodiimide (45 kg) in toluene (35 kg) is added over 1 hour and the reaction mixture is stirred for a further 5–6 hours. (L)-α-aspartyl-3-cyclohexyl-(L)-alanineamide hydrochloride (75 kg) and triethylamine (80 kg) are added to the mixture and stirring is continued for about 2 hours. The reaction mixture is diluted with water (370 kg). The resulting slurry is filtered, the filter cake is washed with water (30 kg) and the combined filtrates are transferred into a 2300 liter stainless steel reactor. Ethyl acetate (347 kg) is added to the solution. After decantation of the organic phase, the aqueous phase is acidified with hydrochloric acid (515 kg) and extracted with ethyl acetate (347 kg). The organic phase is washed twice with 20% aqueous ammonium chloride (109 kg) and concentrated in vacuo. Acetonitrile (1560 kg) and water (45 kg) are added, the solution is heated to about 75° C. and dicyclohexylamine (35 kg) is added over 1 hour. The solution is seeded with N-[N-ethyl-N-[1-oxo-4-[1-[(phenylmethoxy)carbonyl]-4-piperidinyl]butyl]glycyl]-(L)-α-aspartyl-3cyclohexyl-(L)-alanineamide and maintained for one hour at 75° C. The suspension is then cooled to 20° C. over 6 hours and filtered. The filter cake is washed three times with acetonitrile (100 kg) and dried under reduced pressure at about 40° C. to give the title compound (125 kg) as the dicyclohexylamine salt.

Step2: N-[N-ethyl-N-[1-oxo-4-(4-piperidinyl)butyl]glycyl]-(L)-α-aspartyl-3-cyclohexyl-(L)-alanineamide After a thorough nitrogen purge of an hydrogenator, a suspension of N-[N-ethyl-N-[1-oxo-4-[1-[(phenylmethoxy) carbonyl]-4-piperidinyl]butyl]glycyl-(L)-α-aspartyl-3-cyclohexyl-(L)-alanineamide dicyclohexylamine (124 kg) and wet palladium on charcoal (2 kg, 50% wet, 5%) in a mixture of absolute ethanol (440 kg) and purified water (42 kg) is hydrogenated at about 25° C. under 2 bar pressure of hydrogen for 1 hour. After a nitrogen purge, the catalyst is filtered and washed with a mixture of absolute ethanol (65 kg) and purified water (5 kg). The filtrate is heated to about 60° C., acetone (425 kg) is added and the mixture is seeded with N-[N-ethyl-N-[1-oxo-4-(4-piperidinyl)butyl]glycyl]-(L)-α-aspartyl-3-cyclohexyl-(L)-alanineamide (1.1 kg). The suspension is cooled to 20° C. and filtered on an agitated filter dryer. The filter cake is washed with absolute ethanol (100 kg) and dried in vacuo at about 40° C. to give the title compound (61 kg) as a white crystalline solid.

Method C

Step 1: N-ethyl-N-[1-oxo-4-(4-pyridinyl)butyl]glycyl-(L)-α-aspartyl-(L)-phenylalaninamide phenylmethyl ester In a 1 L flask under $N_2$ a solution of 15.1 g (0.06 mole) of N-ethyl-N-[1-oxo-4-(4-pyridinyl)butyl]glycine in 200 mL of dichloromethane is prepared and cooled to 1° C. A solution of 6.95 mL (0.055 mole) of tert-butyl chloroformate in 25 mL of dichloromethane is prepared, cooled to 1° C., and added dropwise over 45 minutes while maintaining the reaction mixture temperature at 1° C. The mixture is stirred at 1° C. for 3 hours. In a separate 800 mL vessel 20 g (0.0498 mole) of L-α-aspartyl-(L)-phenylalaninamide phenylmethyl ester mono(hydrochloride) is dissolved in 200 mL dichloromethane and the mixture is treated by dropwise addition with 15.8 mL (0.11 mole) of triethylamine, affording a solution which is added over 1 hour to the anhydride prepared above at 1° C. The mixture is stirred at −2° C. for 1 hour, then is washed with 250 mL of water, 250 mL of saturated aqueous sodium bicarbonate, 250 mL of 0.14M aqueous hydrochloric acid, then 250 mL of water. The organic phase is checked by HPLC for the presence of unreacted starting material, and the washing cycle is repeated until no further reduction in the corresponding HPLC peaks is observed. The organic layer is dried over magnesium sulfate, filtered, then concentrated in vacuo, and the residual oil is placed under vacuum to maximize solvent removal to afford 23.5 g (79.3% yield; 96.8% analytically pure) of N-ethyl-N-[1-oxo-4-(4-pyridinyl)butyl]glycyl-(L)-α-aspartyl-(L)-phenylalaninamide phenylmethyl ester.

Step 2: N-ethyl-N-[1-oxo-4-(4-piperidinyl)butyl]glycyl-(L)-α-aspartyl-3-cyclohexyl-(L)-alanineamide To a solution of 76 mg N-ethyl-N-[1-oxo-4-(4-pyridinyl) butyl]glycyl-(L)-α-aspartyl-(L)-phenylalaninamide phenylmethyl ester (0.126 mmole) in 1 mL of 9:1 isopropanol/water is added 6 mg of $Pt_2O \cdot H_2O$ (79–84% Pt), then 1.6 μL 1 N aqueous hydrochloric acid. The mixture is agitated and expos hydrogen at 4 Bars at 23° C. for 5 hours 40 minutes, then for 1 hour 45 minutes at 60° C. The mixture is filtered and the filtrate is analyzed by HPLC to show a 100% consumption of starting material to afford N-ethyl-N-[1-oxo-4-(4-piperidinyl)butyl]glycyl-(L)-α-aspartyl-3-cyclohexyl-(L)-alanineamide with traces of N-ethyl-N-[1-oxo-4-(4-pyridinyl)butyl]glycyl-(L)-α-aspartyl-(L)-phenylalaninamide cyclohexylmethyl ester.

Method D

Step 1: N-ethyl-N-[1-oxo-4-[1-[(phenylmethoxy)carbonyl]-4-piperidinyl]butyl]glycyl]-(L)-α-aspartyl-(L)-phenylalaninamide phenylmethyl ester To a solution of 11.1 g (28.4 mmole) of N-ethyl-N-[1-oxo-4-[1[(phenylmethoxy)carbonyl]-4-piperidinyl]butyl] glycine in 44 mL of ethyl acetate is added 6.13 g (28.7 mmole) of solid dicyclohexylcarbodiimide while maintaining the temperature between 25° C. and 33° C., during which time a precipitate forms (dicyclohexyl urea).

In a separate vessel a suspension of 10.97 g (27 mmole) of L-α-aspartyl-(L)-phenylalaninamide phenylmethyl ester mono(hydrochloride) in 88 mL ethyl acetate is treated with 4.2 mL (29.7 mmole) of triethylamine. The mixture is stirred for 15 minutes, giving simultaneous dissolution of the dipeptide and precipitation of triethylamine hydrochloride. The suspension is added to the suspension of activated N-ethyl-N-[1-oxo-4-[1-[(phenylmethoxy)carbonyl]-4piperidinyl]butyl]glycine prepared above while maintaining the temperature between 27° C. and 29° C. The mixture is stirred for 1 hour, during which time the suspension becomes thick. An additional 100 mL of ethyl acetate is added and the mixture is stirred for an additional 1 hour. A 60 mL portion of water is added, giving a mixture of two easily stirrable liquid phases and suspended solid dicyclohexyl urea, which is filtered. The filtrate is washed with 60 mL of saturated aqueous sodium bicarbonate, 60 mL of 1N aqueous hydrochloric acid, and 60 mL of saturated aqueous sodium chloride, then the organic phase is dried over sodium sulfate. The mixture is filtered and concentrated in vacuo and the residue is heated at 50° C. under 1 mm Hg to afford 17.6 g of N-ethyl-N-[1-oxo-4-[1[(phenylmethoxy) carbonyl]-4piperidinyl]butyl]glycyl-(L)-α-aspartyl-(L)-phenylalaninamide phenylmethyl ester. A 400 mg sample is loaded on to prewashed (2 N aqueous hydrochloric acid, water, then 1:1 water/ethanol) Dowex 50WX2 (10 g) and collected by elution with 50 mL 70/30 ethanol/water, then on prewashed (2N sodium hydroxide, water, then 1:1 ethanol/water) Amberlyst A26 ( 10 g), eluting with 50 mL 70:30 ethanol/water. The product-containing eluant is concentrated in vacuo followed by further solvent removal under vacuum at 50° C. (5 mm Hg) to give 350 mg of N-ethyl-N-[1-oxo-4-[1-[(phenylmethoxy)carbonyl]-4-piperidinyl]butyl] glycyl]-(L)-α-aspartyl-(L)-phenylalaninamide phenylmethyl ester.

Step 2: N-ethyl-N-[1- oxo-4-(4-piperidinyl)butyl]glycyl-(L)-α-aspartyl-3-cyclohexyl-(L)-alanineamide In a dry 2 mL sapphire NMR tube is placed 25 mg (0.03 mmole) N-ethyl-N-[1-oxo-4-[1-[(phenylmethoxy) carbonyl]-4piperidinyl]butyl]glycyl-(L)-α-aspartyl-(L)-phenylalaninamide phenylmethyl ester, 12 mg of $PtO_2 \cdot H_2O$ (79–84% Pt) and 1 mL of 85/12 v/v acetic acid/2N aqueous hydrochloric acid. The mixture is agitated under 4 Bars of hydrogen at ambient temperature for 5 hours. The mixture is then filtered using a Millipore Milex filter. HPLC analysis of the filtrate showed 100% of N-ethyl-N-[1-oxo-4-(4-piperidinyl)butyl]glycyl-(L)-α-aspartyl-3cyclohexyl-(L)-alanineamide.

Method E

In a 100 mL flask equipped with a magnetic stirrer is placed 1.12 g (1.51 mmole) of N-ethyl-N-[1-oxo-4-[1 [(phenylmethoxy)carbonyl]-4-piperidinyl]butyl]glycyl-(L)-α-aspartyl-(L)-phenylalaninamide phenylmethyl ester, 107 mg of 5% Pd/C, and 10 mL of 9:1 2-propanol/water. The vessel is purged with argon at 40° C., then the mixture is heated to 50° C. with vigorous agitation and the vessel is purged several times with hydrogen. The mixture is agitated at 50° C. under hydrogen at 1 Bar pressure for 5 hours, then is cooled to ambient temperature, filtered and the filtrate is concentrated in vacuo to afford 713 mg (90% yield) of N-ethyl-N-[1-oxo-4(4-piperidinyl)butyl]glycyl-L-α-aspartyl-(L)-phenylalaninamide. A 50 mg portion is placed, along with 50 mg of Rh/Al$_2$O$_3$ (Engelhard) and 1 mL of acetic acid in a glass ampule, and the mixture is agitated for 17 hours at 80° C. under hydrogen at 4 Bar pressure. HPLC analysis shows 100% by area of N-ethyl-N-[1-oxo-4-(4-piperidinyl)butyl]glycyl-(L)-α-aspartyl-3-cyclohexyl-(L)-alanineamide.

Method F

N-ethyl-N-[1-oxo-4-(4-piperidinyl)butyl]glycyl-(L)-α-aspartyl-3-cyclohexyl-(L)-alanineamide is prepared using the procedure of Method A above, except substituting N-ethyl-N-[1-oxo-3-[1-(phenylmethoxycarbonyl)-4-piperidinylmethylene]propyl]glycine for N-ethyl-N-[1-oxo-4-[1-[(phenylmethoxy)carbonyl]-4-piperidinyl]butyl]glycine.

EXAMPLE 2

Preparation of N-[N-ethyl-N-[1-oxo-4-piperidinyl]butyl]glycyl-(L)-α-aspartyl-3-cyclohexyl-(L)-alanine Step 1: N-[N-ethyl-N-[1-oxo-4-[1-[(phenylmethoxy)carbonyl]-4piperidinyl]butyl]glycyl]-(L)-α-aspartyl-3-cyclohexyl-(L)-alanine bisphenylmethyl ester To a stirred suspension of N-ethyl-N-[1-oxo-4-[1-[(phenylmethoxy)carbonyl]-4-piperidinyl]butyl]glycine (0.858 g, 1.5 mmol) in 4 g of dimethylformamide at 5° C. is added 2-(1 H-) benzotriazole-1-yl)-1.1.3.3-tetramethyluronium tetrafluoroborate (0.482 g, 1.5 mmol) in a single portion and the mixture is stirred for 3 minutes at 5° C. Diisopropylethylamine (0.482 g, 1.5 mmol) is added and the resulting heterogeneous mixture is added via Pasteur pipette to a solution of 0.755 g (1.5 mmol) of (L)-α-aspartyl-3-cyclohexyl-(L)-alanine bisphenylmethyl ester mono (hydrochloride) in 4 g of dimethylformamide. An additional 1 g of dimethylformamide is used for the rinse and an additional portion of 0.16 g (0.5 mmol) of diisopropylethylamine is added to make the mixture slightly basic. The cooling bath is removed and the suspension is stirred at ambient temperature for 20 hours. The resulting orange, heterogeneous mixture is partitioned between methyl tert-butyl ether and H$_2$O. The aqueous phase is extracted with methyl tert-butyl ether. The combined organic phases are washed successively with 1N aqueous HCl, water, saturated aqueous NaHCO$_3$ and brine, dried over MgSO$_4$ and concentrated in vacuo to afford N-[N-ethyl-N-[1-oxo-4-[1-[(phenylmethoxy)carbonyl]-4-piperidinyl]butyl]glycyl]-(L)-α-aspartyl-3-cyclohexyl-(L)-alanine bisphenylmethyl ester (1.21 g) as an amber resin. m/z (ion spray) mlz 839 (M+H)$^+$.

Step 2: N-[N-ethyl-N-[1-oxo-4-piperidinyl]butyl]glycyl-(L)-α-aspartyl-3-cyclohexyl-(L)-alanine A solution of 10.23 g (12.2 mmole) of N-[N-ethyl-N-[1-oxo-4-[1-[(phenylmethoxy)carbonyl]-4-piperidinyl]butyl]glycyl-(L)-α-aspartyl-3-cyclohexyl-(L)-alanine bisphenylmethyl ester in 200 mL of 90% v/v 2-propanol/water is poured over 2 g of 5% Pd/C (Degussa type E101 NO/W, 50% water by weight) in a 500 mL Parr Shaker bottle. The mixture is shaken overnight at 40–50 psi hydrogen and then filtered. The filtrate is concentrated to give N-[N-ethyl-N-[1-oxo-4-piperidinyl]butyl]glycyl-(L)-α-aspartyl-3-cyclohexyl-(L)-alanine (6.47 g) as a glassy solid. MS (ion spray) m/z 525 (M+H)$^+$.

EXAMPLE 3

Preparation of N-[N-ethyl-N-[1-oxo-4-(4-piperidinyl)butyl]glycyl]-(L)-α-aspartyl-4-cyclohexyl-2-(L)-aminobutanoic acid.

Step 1: N-[N-ethyl-N-[1-oxo-4-[1-[(phenylmethoxy)carbonyl]-4-piperidinyl]butyl]glycyl]-(L)-α-aspartyl-4-cyclohexyl -2-(L)-aminobutanoic acid bisphenylmethyl ester To a magnetically stirred 0–5° C. solution of 26.38 g (44.4 mmole) of N-ethyl-N-[1-oxo-4-[1-[(phenylmethoxy)carbonyl]-4-piperidinyl]butyl]glycine in 70 mL of dimethyl formamide is added 15.7 g (48.8 mmole) of 2-(1H-benzotriazole-1-yl)1,1,3,63-tetramethyluronium tetrafluoroborate followed by dropwise addition of 12.9 g (99.6 mmole) of diisopropylethylamine. The resulting solution is poured into a suspension of 19 g (48.4 mmole) of L-α-aspartyl-4-cyclohexyl-2-(L)-aminobutanoic acid bisphenylmethyl ester mono(trifluoroacetate) in 20 mL of dimethyl formamide at to 0–5° C. The resulting mixture is removed from cooling and allowed to stir at 23° C. overnight, to give a homogeneous solution. The mixture is diluted with water, which causes an orange oil to separate. Methyl tert-butyl ether and water are added, the organic layer is removed, and the aqueous layer is extracted twice with methyl tert-butyl ether. The combined organic layers are washed twice with 1N aqueous hydrochloric acid, twice with 1N aqueous sodium hydroxide, and twice with brine, dried over magnesium sulfate, filtered, and concentrated in vacuo to give an oil which is left under high vacuum for two days. The oil (33.4 g) is purified by silica gel (80% ethyl acetate-heptane) to give N-[N-ethyl-N-[1-oxo-4-[1[(phenylmethoxy)carbonyl]4-piperidinyl]butyl]glycyl]-(L)-α-aspartyl-4-cyclohexyl-2-(L)-aminobutanoic acid bisphenylmethyl ester (27.8 g, 73%).

Step 2: N-[N-ethyl-N-[1-oxo-4-(4-piperidinyl)butyl]glycyl]-(L)-α-aspartyl-4-cyclohexyl-2-(L)-aminobutanoic acid A solution of 1.2 g (1.4 mmole) of N-[N-ethyl-N-[1-oxo-4-[1-[(phenylmethoxy)carbonyl]-4-piperidinyl]butyl]glycyl]-(L)-α-aspartyl-4cyclohexyl -2-(L)-aminobutanoic acid bisphenylmethyl ester, prepared as in step 1, in 12 mL of dioxane is poured into a 500 mL Parr Shaker bottle containing 83 mg of 10% Pd/C in 5 mL of water and 3 mL of dioxane. The reaction mixture is shaken overnight at ambient temperature (ca. 23° C.) under 45 psig hydrogen. The mixture is filtered through a bed of celite in a medium sintered glass funnel and the filter cake is washed with a mixture of dioxane and water. The solution is lyophilized and the resulting fluffy white solid is redissolved in a minimum amount of water and lyophilized again to give the title compound as a fluffy white solid (710 mg, 93%). MS (FAB) m/z 539, 561 (M+Na)$^+$.

EXAMPLE 4

Preparation of N-Ethylglycine ethyl ester trifluoroacetate

Step 1: N-[(1,1-dimethylethoxy)carbonyl]-N-ethylglycine ethyl ester

To a 3° C. solution of 86 g (423 mmole) of N-[(1,1-dimethylethoxy)carbonyl]-N-ethylglycine, 21.4 g (465 mmole) of ethanol and 5.17 g (42.3 mmole) of 4-dimethylaminopyridine in 600 mL of dichloromethane is added 47 g (46.2 mmole) of triethylamine, followed by portionwise addition of 89.1 g (46.5 mmole) of 3-N,N-dimethylaminopropylethylcarbodiimide hydrochloride. The stirred mixture is allowed to warm to ambient temperature and stir overnight. The reaction mixture is washed with water, saturated aqueous sodium bicarbonate and brine, dried over magnesium sulfate, filtered, and concentrated in vacuo to give N-[(1,1-dimethylethoxy)carbonyl]-N-ethylglycine ethyl ester (88 g) as an oil. MS (FAB) 232 $(M+H)^+$.

Step 2: N-Ethylglycine ethyl ester trifluoroacetate

A stirred solution of 30.8 g (113 mmole) of N-[(1,1-dimethylethoxy)carbonyl]-N-ethylglycine ethyl ester in 50 mL dichloromethane at 3° C. is treated with 200 mL of 1:1 (volume/volume) trifluoroacetic acid in dichloromethane. The reaction mixture is stirred for 2 hours while warming to ambient temperature. The reaction mixture is concentrated in vacuo and the residual highly mobile oil is subjected to high vacuum to give the desired compound (55.2 g), which is used without further purification.

EXAMPLE 5

Preparation of N-ethylglycine.

To a 5° C. mixture under nitrogen of ethylamine (25 kg) and isopropanol (100 kg) in a 250 liter glass lined reactor is added a solution of glyoxylic acid (25 kg) in isopropanol (25 kg) over 2–3 hours and the solution is hydrogenated with palladium on charcoal (50% wet, 5%, 2.5 kg) over 3 hours under 50 mbar of hydrogen. The reaction mixture is then filtered and the filtrate is concentrated. Isopropanol (80 kg) is added to the slurry and the solid is filtered, washed twice with isopropanol (7 kg), and dried in vacuo at about 40° C. to give N-ethylglycine (21 kg) as a white crystalline solid.

EXAMPLE 6

Preparation of N-ethyl-N-[1-oxo-4-[1-[(phenylmethoxy)carbonyl]-4-piperidinyl]butyl]glycine Method A Step 1: 1-[(Phenylmethoxy)carbonyl]-4-piperidinebutanoic acid To 100 g (622 mmole) of diethyl malonate at 25° C. is added 88 g (272 mmole) of 21% (w/w) ethanolic sodium ethoxide over 20 minutes while maintaining the temperature at 23–25° C. The mixture is stirred for 10 minutes, and 26.18 g (248 mmole) of 4-vinylpyridine is added. The mixture is heated to 85° C. and stirred for 3 hours and then stirred for 15 hours at room temperature. The reaction mixture is concentrated at 44° C. to remove ethanol and the resulting yellow oil is subjected to high vacuum to remove residual solvent. The oil is partitioned between methyl tert-butyl ether and 2.2N aqueous HCl. The aqueous phase is adjusted to pH 6 with 2N aqueous sodium hydroxide. The layers are separated and the organic phase is washed twice with brine. The organic phase is then extracted with 2.2N aqueous HCl (3x). The combined aqueous extracts are heated at reflux overnight. The resulting solution (225 mL, presumed 248 mmole) is poured over 2.5 g of platinum oxide hydrate in a 500 mL Parr Shaker bottle and shaken overnight under 47–55 psi of hydrogen. The mixture is filtered and the filtrate is cooled to 10° C. and treated with 417 mL of aqueous sodium hydroxide while maintaining the reaction temperature at or below 10° C. to achieve a pH of 14 (ca. 40 minutes required). To the stirred mixture is added 100 mL of tetrahydrofuran, followed by the addition over 30 minutes of 68 g (273 mmole) of benzyl-N-succinimidyl carbonate in 150 mL of tetrahydrofuran, while maintaining the temperature at 8° C. The mixture is warmed to ambient temperature and stirred overnight. The mixture is extracted with methyl tert-butyl ether (3x), ethyl acetate, methyl tert-butyl ether, ethyl acetate, and methyl tert-butyl ether. The aqueous phase is cooled to 5° C., acidified to pH 1.9 by slow addition of 27 mL of concentrated hydrochloric acid, and extracted with methyl tert-butyl ether (3x). The combined organic layers from the extraction are washed with brine, dried with magnesium sulfate, filtered, and concentrated in vacuo to provide 1-[(phenylmethoxy)carbonyl]-4-piperidinebutanoic acid (42 g, 55% yield from vinyl pyridine). MS (FAB) m/z 306.

Step 2: N-ethyl-N-[1-oxo-4-[1-[(phenylmethoxy)carbonyl]-4-piperidinyl]butyl]glycine ethyl ester To a stirred, 3° C. solution of 40.7 g (133.3 mmole) of 1-[(phenylmethoxy)carbonyl]-4-piperidinebutano acid in 667 mL of dichloromethane is added 0.5 mL of dimethyl formamide and, dropwise, 66.8 mL of 2M oxalyl chloride in dichloromethane. The reaction mixture is maintained at 3–4° C. during the addition, then stirred at that temperature overnight. The reaction mixture is concentrated in vacuo. The resulting honey colored oil and 133.3 mmole N-ethylglycine ethyl ester trifluoroacetate are dissolved in 250 mL dichloromethane at 3° C. To the stirred mixture is added 52.84 g (408 mmole) of diisopropylethylamine. The mixture is allowed to warm to ambient temperature with stirring over 2 hours, at which point HPLC shows complete reaction. The reaction mixture is concentrated in vacuo, and the resulting oil is dissolved methyl tert-butyl ether. The methyl tert-butyl ether solution is washed with water (2x) and the combined water layers are extracted with methyl tert-butyl ether. The combined organic solutions are washed with 1N aqueous sodium hydroxide (3x) brine (2x), dried over magnesium sulfate and concentrated in vacuo to give N-ethyl-N-[1-oxo-4-[1-[(phenylmethoxy)carbonyl]-4-piperidinyl]butyl]ethyl ester (46.69 g), which is used without further purification. MS (FAB) m/z 419 $(M+H)^+$.

Step 3: N-ethyl-N-[1-oxo-4-[1-[(phenylmethoxy)carbonyl]-4-piperidinyl]butyl]glycine To a solution of 46.7 g (112 mmole) of N-ethyl-N-[1-oxo-4-[1-[(phenylmethoxy)carbonyl]-4-piperidinyl]butyl] glycine ethyl ester in tetrahydrofuran at ambient temperature is added 200 mL of 1N aqueous sodium hydroxide, and the heterogeneous mixture is stirred vigorously for 1 hour. The reaction mixture is concentrated in vacuo and the residual aqueous mixture is diluted with water and extracted with methyl tert-butyl ether (3x). The aqueous layer is acidified to pH 3 with potassium bisulfate, causing an oil to form. The mixture is extracted with methyl tert-butyl ether (3x). The combined organic layers are washed with brine (2x), dried over magnesium sulfate, filtered, and concentrated in vacuo. The resulting oil is subjected to high vacuum to give N-ethyl-N-[1-oxo-4-[1-[(phenylmethoxy)carbonyl]-4-piperidinyl]butyl]glycine (35.5 g). MS (FAB) 391 $(M+H)^+$.

Method B

To a 0° C. solution of 2.1 g (6.88 mmole) of 1-[(phenylmethoxy)carbonyl]-4-piperidinebutanoic acid, in 36 mL of dichloromethane is added 3.6 mL of 2M oxalyl chloride in dichloromethane and 0.25 mL of dimethylformamide. The reaction mixture is stirred at 0° C. for 2.5 hours. The reaction mixture is concentrated in vacuo, and the residue is azeotroped twice with toluene.

An aqueous solution of 2.06 g (19.9 mmole) of N-ethylglycine in 18.7 mL water is chilled to 5° C. and 3.78 g (35 mmole) of solid sodium carbonate is added portionwise, followed by a solution of 6.88 mmole (crude, assumed) of 1-[(phenylmethoxy)carbonyl]-4-piperidinebutanoic acid chloride in 8 mL of tetrahydrofuran. The mixture is warmed to ambient temperature and stirred overnight. The reaction mixture is diluted with water, and extracted with ethyl acetate (3x). The aqueous phase is acidified to pH12 with aqueous potassium bisulfate and extracted with methyl tert-butyl ether. The organic layer is concentrated in vacuo to afford 2.21 g of an oil (MS correct for desired product). The oil is purified using preparative reverse phase HPLC (C-18, 2"×250 cm, 15µ particle size, 300 angstrom pore size) using aqueous acetonitrile doped with 0.1% v/v trifluoroacetic acid, over a gradient of 36–45% acetonitrile. The product-containing fractions are pooled and the solution is frozen and lyophilized. The resulting oil is taken up in ethyl acetate, the solution is concentrated in vacuo, and the resulting oil is subjected to high vacuum to give N-ethyl-N-[1-oxo-4-[1-[(phenylmethoxy)carbonyl]-4-piperidinyl]butyl]glycine (1.01 g, 36% yield). MS (FAB) m/z 391 (M+H)$^+$.

Method C

Step 1: 2-(4-pyridyl)ethylmalonic acid diethyl ester hydrochloride

A mixture under nitrogen of 20% sodium ethoxide in ethanol (263.2 kg) and diethyl malonate (703 kg) in a 1600 liter glass lined reactor is distilled at atmospheric temperature to a temperature of 108° C. 4-vinylpyridine (80.5 kg) is added over 3 hours and the reaction mixture is stirred for 4 hours. Th reaction mixture is then cooled to ambient temperature and water (358 kg) is added over about 1 hour. The pH is adjusted to 4.5 with 33% aqueous hydrochloric acid, and the aqueous layer is extracted with methyl tert-butyl ether (216 kg). Water (357.5 kg) is then added and the biphasic mixture is acidified to pH 1 with 16.5% aqueous hydrochloric acid (29.6 kg). The layers are separated and the aqueous solution of 2-(4-pyridyl)ethylmalonic acid diethyl ester hydrochloride is used as-is.

Step 2: 4-(4-pyridyl)butanoic acid hydrochloride

The aqueous solution of 2-(4pyridyl)ethylmalonic acid diethyl ester hydrochloride prepared in step 1 is distilled at atmospheric pressure to a temperature of 105° C. to remove methyl tert-butyl ether and ethanol, and 33% aqueous hydrochloric acid (67 kg) is added over 50 minutes. The reaction mixture is stirred for about 6 hours at about 105° C. and then concentrated to obtain about 530 kg of distillate. The mixture is allowed to cool to 60° C. and acetic acid (591 kg) is added. Distillation is continued under reduced pressure (10 mmHg) in order to obtain a level of 6.6% of water in the reaction mixture. To the slurry is added acetone (374 kg), and the suspension is cooled to 15° C over 3 hours. The slurry is stirred at 15° C. for 1 hour and the precipitate is filtered, washed twice with acetone (94 kg) and dried in vacuo for 24 hours at 40° C. to give 4-(4-pyridyl)butanoic acid hydrochloride (126 kg). The solid is then dissolved in water (300 kg) to give a 30% w/w aqueous solution which is used as is in step 3.

Step 3: 4-(4-piperidyl)butanoic acid hydrochloride

To the 30% aqueous solution of 4-(4-pyridyl)butanoic acid hydrochloride prepared in step 2 (208.9 kg) and water (145 kg) is added platinum on charcoal (50% wet, 5%, 2.52 kg). The mixture is hydrogenated at about 70° C. under atmospheric pressure over 15 hours and then allowed to cool to ambient temperature. The catalyst is filtered and washed with water (20 kg). The resulting aqueous 16% solution of 4-piperidinebutanoic acid hydrochloride (388.5 kg) is used as is in step 4.

Step 4: 1-[(Phenylmethoxy)carbonyl]-4-piperidinebutanoic acid

Either solid 4-(4-piperidyl) butyric acid hydrochloride (124 kg) is dissolved in water (600 kg), or the 16% aqueous solution of 4-(4-piperidyl)butyric acid hydrochloride prepared in step 3 (777 kg), is diluted with aqueous sodium hydroxide (289 kg) in a 1600 liter glass lined reactor cooled at 5° C. Benzylchloroformate (112 kg) is added over a period of 2–3 hours and the solution is heated to about 25° C. The reaction mixture is extracted with methyl tert-butyl ether (476 kg). The aqueous layer is then acidified with hydrochloric acid (187 kg) and extracted with toluene (450 kg). The organic layer is washed with water (240 kg) and dried by azeotropic distillation at atmospheric pressure under nitrogen. The resulting solution of 1-[(phenylmethoxy) carbonyl]-4-piperidinebutanoic acid in toluene is used as is in step 5. Weight of the product in solution: 179 kg. Quality: about 35% w/w in toluene.

Step 5: N-ethyl-N-[1-oxo-4-[1-[(phenylmethoxy)carbonyl]-4-piperidinyl]butyl]gylcine dicyclohexylamine To the solution of 1-[(phenylmethoxy)carbonyl]-4-piperidinebutanoic acid in toluene prepared in step 4 (253 kg) under nitrogen is added thionyl chloride (42 kg). The reaction mixture is diluted with methyl tert-butyl ether (85 kg) and stirred for about 24 hours at approximately 15° C. in a 630 liter glass lined reactor. This solution is added to a biphasic mixture of water (177 kg), 30% aqueous sodium hydroxide (227 kg), N-ethyl glycine (36 kg) and methyl tert-butyl ether (65 kg) in a 1600 liter glass lined reactor over 4–5 hours and the mixture is stirred for about 30 minutes. The biphasic mixture is then diluted with water (100 kg) and acidified to pH 6.5 with hydrochloride acid. The aqueous phase is washed with methyl tert-butyl ether (65 kg) and ethyl acetate (157 kg) is added to the aqueous phase. The biphasic mixture is acidified to pH 4 with hydrochloric acid (84 kg). The layers are separated and ethyl acetate (385 kg) is added to the organic phase. The organic phase is heated to about 60° C. and a solution of dicyclohexylamine (63 kg) in ethyl acetate (230 kg) is added. The mixture is seeded and cooled to about 10° C. The solid is filtered, washed twice with ethyl acetate (150 kg) and dried in vacuo at about 40° C. to give the title compound (139 kg) as a white crystalline solid.

EXAMPLE 7

Preparation of N-ethyl-N-[1-oxo-4-(4-pyridinyl)butyl]glycine

Step 1: N-ethyl glycine phenylmethyl ester mono (hydrochloride)

To 250 mL of a 2M solution of ethylamine in tetrahydrofuran is added 47.2 g (0.2 mole) of benzyl bromoacetate in 50 mL of tetrahydrofuran over 0.5 hours while maintaining the reaction temperature at 22 ° C. to 26° C. The reaction mixture is then cooled to 2° C., at which point ethylamine hydrobromide crystallizes and is collected by filtration. The filtrate is concentrated in vacuo at 30° C. to afford 39.4 g of a yellow residue. The residue is taken up in 350 mL 2-propanol with agitation, giving a white solid, which is collected by filtration. To the filtrate is added with strong agitation 59 mL of 3.6 N hydrochloric acid in 2-propanol, the mixture is stirred, and the resulting white solid is collected by filtration. The residue is dried to afford 32.5 g of solid. This material is triturated with 100 mL of tetrahydrofuran, then 100 mL of 2-propanol and dried to afford 30 g (0.13 mole, 65% yield, 87% analytically pure) of N-ethyl glycine phenylmethyl ester mono(hydrochloride).

Step 2: N-ethyl-N-[1-oxo-4-(4-pyridinyl)butyl]glycine phenyl methyl ester

A solution of 32.5 g (0.16 mole) of 4-pyridine butyric acid and 17.53 mL (0.174 mole) of N-methyl morpholine in 300 mL of dichloromethane under nitrogen is cooled to 0° C., and a precooled (0° C.) solution of 18.75 mL (0.152 mole)

of pivaloyl chloride in 100 mL dichloromethane is added over 0.5 hours while maintaining the reaction mixture at 0° C. In a separate 500 mL flask, 33.5 g (0.145 mole) of N-ethyl glycine phenylmethyl ester mono(hydrobromide) is dissolved in 400 mL of dichloromethane and 35 mL (0.48 mole) of N-methyl morpholine is added. This mixture is added to the activated pyridinebutyric acid solution at −0.5° C. over 2 hours. After 1 hour, the mixture is diluted with water, agitated, and the layers are separated. The organic phase is washed with saturated aqueous sodium bicarbonate, 0.1 M aqueous hydrochloric acid and water, dried over magnesium sulfate, filtered and concentrated in vacuo to afford 46.2 g (0.135 mole, 93% yield) of N-ethyl-N-[1-oxo-4-(4-pyridinyl)butyl]glycine phenyl methyl ester as a yellow oil.

Step 3: N-ethyl-N-[1-oxo-4-(4-pyridinyl)butyl]glycine

A solution of 46 g (0.135 mole) of N-ethyl-N-[1-oxo-4-(4-pyridinyl)butyl]glycine phenyl methyl ester in 300 mL of methanol is added to 4 g of 10% Pd/C (50% water by weight) in a 1L autoclave. The vessel is evacuated three times with vacuum broken to nitrogen, then is evacuated three additional times, with vacuum broken to hydrogen at atmospheric pressure. The vessel is sealed and heated at 25° C. with agitation for 2 hours. The mixture is filtered under nitrogen to give a pale yellow filtrate, which is concentrated in vacuo at 40° C. until a white solid begins to appear. A 150 mL portion of 2-propanol is added, causing a rapid crystallization of product. The mixture is stirred for 0.5 hours, then product is collected by filtration. The solid is washed with 2 40 mL portions of 2-propanol, then dried to afford 19 g of product. The mother liquor is concentrated and the residue taken up in 2-propanol, resulting in formation of a white precipitate. The mixture is stirred for 0.5 hours, then filtered, and the solid is washed with 2-propanol, then dried to afford 5 g of product, for a total yield of 24 g (0.095 mole; 70% yield; 99A% pure) N-ethyl-N-[1-oxo-4-(4-pyridinyl)butyl]glycine.

EXAMPLE 8

Preparation of (L)-α-aspartyl-3-cyclohexyl-(L)-alanineamide phenylmethyl ester trifluoroacetate Step 1: N-[(1,1-dimethylethoxy)carbonyl]-(L)-α-aspartyl-3-cyclohexyl-(L)-alanineamide phenylmethyl ester To a mechanically-stirred, 18° C. solution of 37.5 g (116 mmole) of BOC-β-benzyl-(L)-aspartic acid in 270 mL ethyl acetate is added a solution of 17.75 g (116 mmole) of hydroxybenzotriazole hydrate in 25 mL of dimethylformamide. A solution of 24.5 g (119 mmole) of dicyclohexylcarbodiimide in 50 mL of ethyl acetate is then added over 30 minutes, using a water bath to keep the reaction temperature at or below 25° C. The reaction mixture is stirred for 1 hour, then a syrup of 33 g (116 mmole) of 3-cyclohexyl-(L)-alanineamide ester mono (trifluoroacetate) in 25 mL of dimethylformamide is added at 23° C., followed by dropwise addition of neat N-methylmorpholine over 2 minutes. The reaction mixture is allowed to warm to 30° C. during the N-methylmorpholine addition. The reaction mixture is stirred at ambient temperature overnight. The reaction mixture is filtered to remove dicyclohexyl urea, and the filtrate is diluted with ethyl acetate, washed twice with water, once with brine, twice saturated aqueous sodium bicarbonate, and once with 1:1 0.5N citric acid/brine. The organic phase is dried with magnesium sulfate, filtered, and diluted with heptane. The mixture is allowed to stand overnight, and the resulting crystals are collected by filtration, washed twice with heptane, and dried under vacuum to give a first crop of 37.5 g and a second crop of 9.5 g. Both crops show acceptable HPLC purity and are physically combined to afford 47 g of N-[(1,1-dimethylethoxy)carbonyl]-(L)-α-aspartyl-3-cyclohexyl-(L-alanineamide phenylmethyl ester (85 yield). MS (FAB) m/7 476 (M+H)⁺.

Step 2: (L)-α-aspartyl-3-cyclohexyl-(L)-alanineamide phenylmethyl ester trifluoroacetate To a mechanically-stirred solution of 45.4 g (95.5 mmole) of N-[(1,1-dimethylethoxy)carbonyl]-(L)-α-aspartyl-3-cyclohexyl-(L)-alanineamide phenylmethyl ester in 350 mL of dichloromethane at 20° C. is added 67 g (590 mmole) of trifluoroacetic acid over 15 minutes. The reaction mixture is stirred for 2 hours. The reaction mixture is concentrated in vacuo to afford an orange-yellow oil, which is azeotroped with dichloromethane, then subjected to high vacuum to further minimize residual solvents. The concentrate, an oil, is triturated with 1:1 methyl tert-butyl ether/heptane to give a white solid. The mixture is stirred in methyl tert-butyl ether for 2 hours, then is allowed to stand for 2 days. The crystals are collected by filtration and dried under vacuum to give (L)-α-aspartyl-3-cyclohexyl-(L)-alanineamide phenylmethyl ester mono(trifluoroacetate) (43 g, 92% yield). MS (FAB) m/z 376 (M+H)⁺.

EXAMPLE 9

Preparation of (L)-α-aspartyl-4-cyclohexyl-2-(L)-aminobutanoic acid bisphenylmethyl ester trifluoroacetate Step 1: N-[(1,1-dimethylethoxy)carbonyl]-4-cyclohexyl-2-(L)-aminobutanoic acid phenylmethyl ester A solution of 30 g (107.5 mmole) of N-[(1,1dimethylethoxy)carbonyl]-(L)-homophenyl alanine and 2 mL of acetic acid in 100 mL methanol is poured over 3 g of 5% rhodium/alumina in a 500 mL Parr Shaker bottle. The reaction mixture is shaken overnight under 46–47 psi hydrogen, then filtered under a blanket of nitrogen through Celite 545 in a sintered glass funnel. The celite pad is washed with methanol. The filtrate is concentrated in vacuo at 30° C. The resulting oil is taken up in methyl tert-butyl ether, washed twice with water and once with brine, dried over magnesium sulfate, filtered, and concentrated in vacuo. The residue (presumed 107.5 mmole) is dissolved in 250 mL of dichloromethane, and the solution is treated with 12 g (118.5 mmole) of triethylamine, followed by 18.4 g (107.5 mmole) of benzylchloroformate, during which time a white solid forms. Following the addition of the benzylchloroformate, 1.3 g (10.75 mmole) of 4-dimethylaminopyridine is added in a single portion. The mixture is allowed to stir for 2 hours at 0° C. The mixture is then concentrated in vacuo, the residue is taken up in ethyl acetate, and the solution is washed twice with water, twice with 1N aqueous hydrochloric acid, twice with 1N aqueous sodium hydroxide and once with brine, dried over magnesium sulfate, filtered and concentrated in to give N-[(1,1-dimethylethoxy)carbonyl]-4-cyclohexyl-2-(L)-aminobutanoic acid phenylmethyl ester (33.8 g) as an oil. MS (FAB) m/z 748 (M+Na)⁺.

Step 2: 4-Cyclohexyl-2-(L)-aminobutanoic acid phenylmethyl ester mono(trifluoroacetate)

To a solution of 33 g (88 mmole) of N-[(1,1-dimethylethoxy)carbonyl]-4-cyclohexyl-2-(L)-aminobutanoic acid phenylmethyl ester in 136 mL of dichloromethane is added 136 mL of trifluoroacetic acid over 30 minutes. The reaction temperature remained below 23° C. The mixture is stirred at ambient temperature for 3 hours, then is concentrated in vacuo. The residue is redissolved in dichloromethane and reconcentrated. The resulting mobile oil is taken up in 50 mL of methyl tert-butyl ether and 350 mL of heptane, the solution is seeded, then cooled at −10° C. for 24 hours. A first crop is collected by filtration, washed with heptane, and dried under vacuum (20.1 g). The mother liquor is concentrated in vacuo, then redissolved in 12 mL methyl tert-butyl ether and 84 mL of heptane. This, with seeding and cooling to −10° C. provides a second crop of 5.2 g. The two crops are of comparable HPLC purity, and are physically blended to afford 4-cyclohexyl-2-(L)-aminobutanoic acid phenylmethyl ester mono (trifluoroacetate) (25.7 g, 75% yield). MS (FAB) 276 (M+H)$^+$.

Step 3: N-[(1,1-dimethylethoxy)carbonyl]-(L)-α-aspartyl-4-cyclohexyl-2-(L)-aminobutanoic acid bisphenylmethyl ester To a mechanically-stirred, 18° C. solution of 20.4 g (63 mmole) of BOC-β-benzyl-(L)-aspartic acid in 154 mL of ethyl acetate is added a solution of 9.65 g (63 mmole) of hydroxybenzotriazole hydrate in 12 mL of dimethylformamide. A solution of 13.3 g (64.5 mmole) of dicyclohexylcarbodiimide in 25 mL of ethyl acetate is added over 15 minutes while maintaining the reaction mixture temperature at or below 25° C. The reaction mixture is stirred for 1 hour, then a syrup of 24.5 g (63 mmole) of 4-cyclohexyl-2-(L)-aminobutanoic acid trifluoroacetate in 15 mL of dimethylformamide is added at 18° C., followed by dropwise addition of N-methylmorpholine over 5 minutes. The reaction mixture is allowed to warm to 25° C. during the N-methylmorpholine addition. The reaction mixture is stirred at ambient temperature overnight. The reaction mixture is filtered to remove dicyclohexyl urea, and the filtrate is washed twice with water, twice with saturated aqueous sodium bicarbonate, twice with 0.5N aqueous citric acid and once with brine, dried with magnesium sulfate, filtered, and concentrated in vacuo. The resulting waxy solid is dissolved in methyl tert-butyl ether at 50° C., the solution is filtered hot to remove a small amount of fine white insoluble material, then diluted at 50° C. with heptane. The solution is cooled to ambient temperature and placed in a freezer at −10° C. overnight. The resulting solid is collected by filtration, washed with heptane, and dried in vacuo to afford N-[(1,1dimethylethoxy)carbonyl]-(L)-α-aspartyl-4-cyclohexyl-2-(L)-aminobutanoic acid bisphenylmethyl ester (29.8 g, 81% yield). MS (FAB) m/z 581.

Step 4: (L)-α-aspartyl-4-cyclohexyl-2-(L)-aminobutanoic acid bisphenylmethyl ester mono (trifluoroacetate)

To a mechanically-stirred solution of 28.8 g (49.5 mmole) of N-[(1,1-dimethylethoxy)-carbonyl]-(L)-α-aspartyl-4-cyclohexyl -2-(L)-aminobutanoic acid bisphenylmethyl ester in 300 mL of dichloromethane at 20° C. is added 222 g (1.94 mole) of trifluoroacetic acid over 30 minutes and the reaction mixture is stirred for 3 hours. The reaction mixture is concentrated in vacuo to afford an oil, which is redissolved in dichloromethane and concentrated again. The residue is triturated with 1:1 methyl tert-butyl ether/heptane, to afford a white solid. The solid is collected by filtration and dried in vacuo to give (L)-α-aspartyl-4-cyclohexyl-2-(L)-aminobutanoic acid bisphenylmethyl ester trifluoroacetate (27.4 g, 46 mmole, 92.9% yield). mp 143–144° C.

EXAMPLE 10

Preparation of (L)-α-aspartyl-3-cyclohexyl-(L)-alanine bisphenylmethyl ester hydrochloride Step 1: N-[(1,1-dimethylethoxy)carbonyl]-3-cyclohexyl-(L)-alanine phenylmethyl ester A stirred, milky solution of 25.6 g (94.5 mmole) of N-[(1,1-dimethylethoxy)carbonyl]-3-cyclohexyl-(L)-alanine, 11.2 g (104 mmole) of benzyl alcohol, and 1.15 g (9.45 mmole) of 4-dimethylaminopyridine in a mixture of 210 mL of dimethyl formamide and 150 mL of dichloromethane is cooled to 5° C., and 19.2 g of 3-N,N-dimethylaminopropylethylcarbodiimide hydrochloride is added over 5 minutes. The mixture is then warmed to ambient temperature and is stirred overnight. The reaction mixture is filtered to remove a fine precipitate, and the filtrate is concentrated in vacuo. The residue is taken up in water and extracted with ethyl acetate (3×). The combined organic solutions are washed with 0.5N aqueous citric acid and twice with water, dried over magnesium sulfate, filtered, and concentrated in vacuo. The resulting oil is subjected to high vacuum to minimize volatiles to give N-[(1,1-dimethylethoxy)carbonyl]-3-cyclohexyl-(L)-alanine phenylmethyl ester (35.3 g). MS (ion spray) m/z 362 (M+H)$^+$.

Step 2: 3-cyclohexyl-(L)-alanine phenylmethyl ester mono (trifluoroacetate)

To a stirred solution of 35.3 g (94.5 mmole) of N-[(1,1-dimethylethoxy)carbonyl]-3-cyclohexyl-(L)-alanine phenylmethyl ester in 100 mL of dichloromethane at 17° C. is added 100 mL of trifluoroacetic acid over 15 minutes during which time the reaction mixture temperature rises to 21° C. The reaction mixture is stirred overnight, then is concentrated in vacuo. The residue is azeotroped with dichloromethane, toluene and methyl tert-butyl ether. The resulting oil is subjected to high vacuum to afford 3-cyclohexyl-(L)-alanine phenylmethyl ester trifluoroacetate (32.6 g). MS (ion spray) m/z 262 (M+H)$^+$.

Step 3: N-[(1,1-dimethylethoxy)carbonyl]-(L)-α-aspartyl-3-cyclohexyl-(L)-alanine bisphenylmethyl ester To a mechanically-stirred solution of 27.6 g (85.5 mmole) of BOC-β-benzyl-(L)-aspartic acid in 110 mL of ethyl acetate is added a solution of 13.1 g (85.5 mmole) of hydroxybenzotriazole hydrate in 21.4 mL of dimethylformamide. A solution of 18.15 g (88 mmole) of dicyclohexylcarbodiimide in 80 mL of ethyl acetate is added over 15 minutes while maintaining the reaction mixture temperature at or below 25° C. The reaction mixture was stirred for 1 hour, and a solution of 32 g (85.5 mmole) of 3-cyclohexyl-(L)-alanine phenylmethyl ester trifluoroacetate in 120 mL ethyl acetate is added at 20° C., followed by dropwise addition of 14.6 g of N-methylmorpholine over 5 minutes (final pH 4–5). The reaction mixture is allowed to warm to 25° C. during the N-methylmorpholine addition. The reaction mixture is stirred at ambient temperature overnight. The reaction mixture is filtered to remove dicyclohexyl urea, and the filtrate is washed twice with water, once with 0.5N aqueous citric acid and twice with saturated aqueous sodium bicarbonate, dried with magnesium sulfate, filtered and concentrated in vacuo. The resulting oil is dissolved in methyl tert-butyl ether and the solution is filtered to remove a small amount of fine white insoluble material. The filtrate is concentrated in vacuo and the resulting oil is subjected to high vacuum to give N-[(1,1-dimethylethoxy)carbonyl]-(L)-α-aspartyl-3-cyclohexyl-(L)-alanine bisphenylmethyl ester (32.9 g). MS (ion spray) m/z 566 (M+H)$^+$, 584 (M+Na)$^+$.

Step 4: (L)-α-aspartyl-3-cyclohexyl-(L)-alanine bisphenylmethyl ester mono (hydrochloride)

Hydrochloric acid is bubbled through a 0° C. magnetically-stirred solution of 17 g (30 mmole) of N-[(1,1-dimethylethoxy)carbonyl]-(L)-α-aspartyl-3-cyclohexyl-(L)-alanine bisphenylmethyl ester in 60 g of ethyl acetate for approximately 5 minutes. During this time the temperature of the solution rises from 5° C. to 20° C., then starts to cool back down. The ice bath is removed and the solution is stirred at ambient temperature for 90 minutes. Excess HCl is driven off by bubbling nitrogen through the solution, after which the mixture solidified. Ethyl acetate (100 g) is added to facilitate agitation (thixotropic), and nitrogen is bubbled through the mixture for an additional 3 minutes. The solid material is isolated by filtration on a Buchner funnel. The filter cake is rinsed with ethyl acetate and dried overnight under vacuum (20 mbar) with N$_2$ bleed, to afford (L)-α-aspartyl-3-cyclohexyl-(L)-alanine bisphenylmethyl ester mono hydrochloride (10.7 g) as a white solid. MS (ion spray) m/z 467 (M+H)$^+$.

EXAMPLE 11

Preparation of N-[(1,1-dimethylethoxy)carbonyl]-(L)-α-aspartyl-3-phenyl-(L)-alanineamide Method A To a mechanically-stirred, 38° C. mixture of ethylene glycol (140 g) and methanol (35 g) is added di-tert-butyl dicarbonate (45 g) and aspartame (5 g). Triethylamine (17.5 g) is then added via syringe pump at 0.2 ml/min. Aspartame (5 g) is then added in 9 portions at 12 minute intervals. The reaction temperature is maintained at about 38° C. for 30 minutes. The reaction mixture is degassed under vacuum until no more gas evolution is observed (ca. 20 min.). Ammonia (19 g) is then added under the surface of the reaction mixture via a diptube over 45 minutes and the reaction mixture is heated overnight at about 60° C. The reaction mixture is diluted with water (280 g) and the reaction temperature is adjusted to about 45° C. Acetic acid (55 g) is added to adjust the pH to about 5.9. The mixture is cooled to 40° C. at which time a solid begins to form. The mixture is cooled to 20° C. over 2 hours and acetic acid (250 g) is added to adjust the pH to about 5 and the mixture is stirred for 0.5 hours. The solid is filtered, washed with water (3×), and dried under vacuum at 50° C. to give N-[(1,1-dimethylethoxy)carbonyl]-(L)-α-aspartyl-3-phenyl-(L)-alanineamide (53 g) as a white crystalline solid.

Method B

A mixture of aspartame (25 kg) and di-tert-butyl dicarbonate (22 kg) in methanol (250 kg) in a 400 liter glass lined reactor is heated to about 30° C. and lithium hydroxide (3.6 kg) is added over 30 minutes. The suspension is stirred for about 4 hours and ammonia gas (39 kg) is added under nitrogen. The slurry is stirred for 2 days and then is concentrated in vacuo to eliminate ammonia and methanol. Water (170 kg) and acetic acid (8 kg) are added to the resulting suspension, the precipitate is filtered and the filter cake is washed twice with water (25 kg) and dried in vacuo at about 40° C. to give N-[(1,1-dimethylethoxy)carbonyl]-(L)-α-aspartyl-3phenyl-(L)-alanineamide (29 kg) as a white crystalline solid.

EXAMPLE 12

Preparation of (L)-α-aspartyl-3-cyclohexyl-(L)-alanineamide mono (hydrochloride)

A mixture of N-[(1,1-dimethylethoxy)carbonyl]-(L)-α-aspartyl-3-phenyl-(L)-alanineamide (129 kg) and platinum (IV) oxide (5 kg) or platinum on alumina (wet 50%, 5%, 12 kg) in a 1600 liter glass lined reactor in acetic acid (700 kg) is hydrogenated at about 60° C. under 4 bars of hydrogen for 3–5 hours. The catalyst is filtered and washed with acetic acid (20 kg). Gaseous hydrochloric acid (7.8 kg) is added to 215 kg of the acetic acid solution over a period of 1–2 hours in a 400 liter glass lined reactor under nitrogen. The suspension is stirred for 1 hour and filtered. The filter cake is washed twice with acetic acid (20 kg) and twice with acetone (20 kg) and dried in vacuo at about 40° C. to give (L)-α-aspartyl-3-cyclohexyl-(L) -alanineamide mono (hydrochloride) (31 kg) as a white crystalline solid.

EXAMPLE 13

Preparation of (L)-α-Aspartyl-(L) phenylalaninamide phenylmethyl ester mono (hydrochloride)

Step 1: N-[(1,1-dimethylethoxy)carbonyl]-(L)-α-aspartyl-(L)-phenylalanine methyl ester mono(sodium) salt A 6 L flask is charged with 294.4 g (0.68 mole) of aspartame, 2000 mL of methanol, 2000 mL of water, and 192.96 g (0.88 mole) of di-tert-butyl dicarbonate and the mixture is cooled to 0° C. Aqueous sodium hydroxide (10N, 68.6 mL) is added over a 15 minute period while maintaining the temperature between 0° C. and 4° C. Cooling is then stopped, and the mixture is allowed to warm to ambient temperature and is stirred for 2 days. The clear solution is concentrated in vacuo to afford an oil, which is taken up in 500 mL of ethyl acetate and reconcentrated to afford 297 g of an oil. This is dissolved in 1 L of ethyl acetate at 48° C., affording a clear solution. The solution is allowed to cool to room temperature overnight. The crystallized product is collected by filtration, washed with 400 mL of ethyl acetate, and dried in a vacuum oven to afford 165 g (0.42 mole, 62% yield) of N-[(1,1-dimethylethoxy)carbonyl]-(L)-α-aspartyl-(L)-phenylalanine mono(sodium) salt. Upon reducing the volume of the mother liquors, an additional 95.4 g (0.24 mole) of solid product is obtained. (total yield: 97%)

Step 2. N-[(1,1-dimethylethoxy)carbonyl]-(L)-α-aspartyl-(L)-phenylalaninamide mono(sodium) salt Ammonia (255 g, 15 mole) is condensed in a 4 L flask. In a separate vessel a solution of 260 g (0.659 mole) N-[(1,1-dimethylethoxy)carbonyl]-(L)-α-aspartyl-(L)-phenylalanine methyl ester mono(sodium) salt in 1300 mL of methanol is prepared, and this is added to the ammonia over 0.5 hours at between −32° C. and −5° C. The mixture is warmed to ambient temperature over 3 hours, then is stirred for an additional 2 hours. The methanol is removed in vacuo at 40° C., affording 501 g of a paste. This is taken up in 1 L of ethyl acetate, from which product crystallized. The mixture is diluted with an additional 2 L of ethyl acetate and filtered. The solid is dried under vacuum overnight at ambient temperature, then under vacuum at 50° C. for 1.5 hours to afford 243.5 g (0.645 mole, 98% yield) of N-[(1,1-dimethylethoxy)carbonyl]-(L)-α-aspartyl-(L)-phenylalaninamide mono(sodium) salt.

Step 3: N-[(1,1-dimethylethoxy)carbonyl]-(L)-α-aspartyl-(L)-phenylalaninamide phenylmethyl ester To a 1 L round bottom flask and under nitrogen is added 241 g (0.635 mole) of N-[(1,1-dimethylethoxy)-carbonyl]-(L)-α-aspartyl-(L)-phenylalaninamide mono(sodium) salt and 2500 mL of dimethylformamide and the mixture is stirred until a solution is obtained. Neat benzyl bromide, 75.4 g (0.635 mole) is added over five minutes at 23–26° C. The mixture is stirred at ambient temperature for 21.5 hours, then is diluted slowly with 2500 mL of water, causing a temperature rise to 32° C. The mixture is stirred for 1 hour while cooling to ambient temperature, during which time a solid crystallized. The solid is collected by filtration, washed with three 1 L portions of water and dried at 50° C. for 2 days to afford 232 g (0.495 mmole, 78% yield.) of N-[(1,1-dimethylethoxy)-carbonyl]-(L)-α-aspartyl-(L)-phenylmethyl ester.

Step 4: L-α-Aspartyl-(L)-phenylalaninamide phenylmethyl ester mono(hydrochloride)

A solution of N-[(1,1-dimethylethoxy)-carbonyl]-(L)-α-aspartyl-(L)-phenylalaninamide phenylmethyl ester in 4N hydrogen chloride/ethyl acetate is stirred for 1 hour at ambient temperature. The mixture is then concentrated, and the residue is taken up in 1.1 L of ethyl acetate and stirred overnight. The resulting solid is collected by filtration and dissolved in 3 L of water. The solution is washed with 3 500 mL portions of dichloromethane. The aqueous solution is evaporated in part by rotary evaporation at 55° C. The solution is allowed to cool. A solid crystallizes and is collected by filtration as two crops (113.6 g and 34.1 g), affording a final yield of 147.7 g (0.364 mole, 79% yield) of L-α-Aspartyl-(L)-phenylalaninamide phenylmethyl ester mono(hydrochloride).

EXAMPLE 14

Preparation of N-ethyl-N-[1-oxo-3-[1-(phenylmethoxycarbonyl)-4-piperidinylmethylene] propyl]glycine Step 1: 1-phenylmethoxycarbonyl-4-piperidone A mixture of 40 kg of N-benzyloxycarbonyl) succinimide and 26 kg (175 mol) of 4-piperidone hydrochloride hydrate in 38.8 kg of water and 88 kg of tetrahydrofuran is stirred at about 15° C. until dissolution is complete (~15 minutes). N-methylmorpholine (22.8 kg) is added to the agitated mixture (exothermic) while maintaining the temperature at or below 20° C. The reaction mixture is agitated at about 20° C. for 2.5 hours, at which point HPLC indicates complete reaction. The mixture is diluted with 115.2 kg of methyl tert-butyl ether and 38.8 kg of water and is agitated at about 20° C. for 5 minutes. Agitation is stopped, the layers are allowed to separate, and the aqueous (lower) layer is removed and discarded. The organic layer is washed twice with 129.6 kg of water (agitate 5 minutes, separate phases, remove/discard aqueous [lower] phase). The organic layer is washed with 5.2 kg of NaCl in 46.8 kg of water (agitate 5 minutes, separate phases, remove/discard aqueous [lower] layer). The organic layer is treated with 11.5 kg of MgSO$_4$, with agitation for 1 hour, then the mixture is filtered. The reactor is rinsed with 8 kg of methyl tert-butyl ether (filtered, combined with main filtrate; total filtrate water content: 0.52%). The filtrate volume is reduced by half via distillation at reduced pressure at 30° C. Vacuum is broken to nitrogen and the residue is cooled to 20° C. (pot residue water content: 0.43%). The residue is diluted with 57.6 kg of methyl tert-butyl ether, then mixture volume is reduced again by half via distillation under vacuum at 30° C. Vacuum is released to nitrogen and the mixture is cooled to 20° C. (pot residue water content: 0.25%). This is repeated 5 additional times. The final pot residue is diluted with 28.8 kg of methyl tert-butyl ether and mixed for 5 minutes, then assayed for water content and content of 1-phenylmethoxycarbonyl-4-piperidone (water: 0.05%; wt/wt assay 1-phenylmethoxycarbonyl-4-piperidone: 22.66 wt%, 35.36 kg, 155 mole, 88.6% yield.).

Step 2: 3-(1-phenylmethoxycarbonyl-4-piperidinylmethylene)propanoic acid

To a suspension of 82 g of 3-carboxypropyl triphenylphosphonium bromide in 407 mL of 1,2-diethoxyethane at 14° C. is added over 25 minutes 220 g of 20 wt % potassium tert-butoxide in tetrahydrofuran while maintaining the reaction mixture temperature at 24–28° C. The mixture is stirred for 1 hour, cooled to 10° C., and a solution of 52.5 g of 1-phenylmethoxycarbonyl-4-piperidone in 246 mL of methyl tert-butyl ether is added over 30 minutes while maintaining cooling. After addition is complete, the mixture is stirred at 12° C. for 10 minutes, then warmed to 20° C. and stirred for an additional 30 minutes. The reaction mixture is treated with 410 mL of 1N aqueous HCl for 10 minutes, diluted with 328 mL of methyl tert-butyl ether, and then the phases are separated. The organic phase is washed with 205 mL of water, then 210 mL of 1N aqueous NaOH. The NaOH layer, which contains the product, is collected separately, washed with three 189 g portions of ethyl acetate, acidified to pH 3.48 with concentrated HCl, then extracted with 189 mL of ethyl acetate. The ethyl acetate layer is separated, washed with 211 mL of water, then dried for 30 minutes over 10 g of MgSO$_4$, filtered, and concentrated in vacuo. The oily residue (50.7 g) is crystallized from toluene/heptane to afford a total of 29.46 g (51% yield) of 3-(1-phenylmethoxycarbonyl-4-piperidinylmethylene)propanoic acid. Mass Spec: M$_{calc.}$ 303, M+1$_{obsvd}$ 304. $^1$H NMR: (δ vs TMS, CDCl$_3$) 2.2, t (2H); 2.25, t (2H); 2.35, m (4H); 3.45, m (4H), 5.15, s (2H); 5.2, m (1H); 7.33, 2 (5H). $^{13}$C NMR (δ vs TMS, CDCl$_3$) 22.43, 28.2, 34.26, 35.66, 44.88, 45.74, 67.20, 122.02, 127.83, 127.95, 128.45, 128.69, 128.90, 136.17, 136.72, 155.34, 178.39

Step 3: N-ethyl-N-[1-oxo-3-[1-(phenylmethoxycarbonyl)4-piperidinylmethylene]propyl]glycine N-ethyl-N-[1-oxo-3-[1-(phenylmethoxycarbonyl)-4-piperidinylmethylene]propyl]glycine is prepared using the method of Example 6, except substituting 3-(1-phenylmethoxycarbonyl-4piperidinylmethylene)propanoic acid for 4-1-phenylmethoxycarbonyl-4-piperidinyl)butanoic acid.

We claim:

1. A process for preparing a pseudotetrapeptide compound of formula

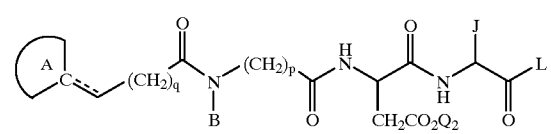

or a salt or prodrug thereof wherein

is optionally nitrogen protected azaheterocyclyl;

----- is a single or double bond;

q is 1–5;

B is alkyl, cycloalkyl, cycloalkylalkyl, alkylcycloalkyl, alkylcycloalkylalkyl, aryl, aralkyl, alkylaryl or alkylaralkyl;

Q$_2$ is H or a carboxylic acid protecting group;

J is —H, alkyl, cycloalkyl, cycloalkylalkyl, alkylcycloalkyl, alkylcycloalkylalkyl, aryl, substituted aryl, aralkyl or substituted aralkyl;

L is OR$^1$, or NR$^1$R$^2$, where R$^1$ and R$^2$ are independently —H, alkyl, cycloalkyl, cycloalkylalkyl, alkylcycloalkyl, alkylcycloalkylalkyl, aryl, aralkyl, alkylaryl, or alkylaralkyl; and p is 1 or 2, comprising (a) coupling an azaheterocyclyl pseudodipeptide of formula $$\underset{B}{\underset{|}{\text{A}}}\overset{\text{(CH}_2)_q}{\diagdown}\underset{B}{\overset{O}{\underset{|}{\text{C}}}}\overset{\text{(CH}_2)_p}{\diagdown}\underset{O}{\overset{}{\text{K,}}}$$

or a salt thereof wherein K is OH or an acyl activating group, with a carboxylic acid substituted dipeptide of formula $$H_2N\diagdown\underset{CH_2CO_2Q}{\overset{O}{\diagdown}}\underset{H}{\overset{}{N}}\diagdown\underset{O}{\overset{J}{\diagdown}}L$$

or a salt thereof,
- (b) optional removing the nitrogen protecting group or carboxylic acid protecting group and
- (c) optionally converting the pseudotetrapeptide to the salt or prodrug.

2. The process of claim 1 wherein $$\underset{}{\overset{\text{A}}{\diagdown}}\diagdown\text{(CH}_2)_q\diagup$$

is a group of formula $$\underset{P_1}{\overset{}{N}}\diagdown N\underset{\diagdown\text{(CH}_2)_n}{\overset{\diagdown\text{(CH}_2)_m}{\diagup}}\diagup$$

wherein
m is 1 to 5;
n is 2–6; and
$P_1$ is a nitrogen protecting group.

3. The process of claim 2 wherein $Q_2$ is a carboxylic acid protecting group.

4. The process of claim 2 wherein
B is alkyl, cycloalkyl, cycloalkylalkyl, alkylcycloalkyl, or alkylcycloalkylalkyl,
J is —H, alkyl, cycloalkyl, cycloalkylalkyl, alkylcycloalkyl, or alkylcycloalkylalkyl,
m is 3, and
n is 3 or 4.

5. The process of claim 2 wherein
B is alkyl,
J is alkyl, cycloalkyl, or cycloalkylalkyl,
$R^1$ and $R^2$ are independently —H, alkyl, cycloalkyl, cycloalkylalkyl, alkylcycloalkyl, alkylcycloalkylalkyl or aralkyl,
m is 3,
n is 3 or 4, and
p is 1.

6. The process of claim 3 wherein $P_1$ is benzyloxycarbonyl and $Q_2$ is benzyl.

7. The process of claim 2 wherein $P_1$ is benzyloxycarbonyl and $Q_2$ is H.

8. The process of claim 6 wherein L is —$NR^1R^2$.

9. The process of claim 7 wherein L is —$NR^1R^2$.

10. The process of claim 1 wherein the salt of the azaheterocyclyl pseudodipeptide is coupled with the salt of the carboxylic acid substituted dipeptide.

11. The process of claim 10 wherein a base addition salt of the azaheterocyclyl pseudodipeptide is coupled with an acid addition salt of the carboxylic acid substituted dipeptide.

12. The process of claim 11 wherein the dicyclohexylamine salt of the azaheterocyclyl pseudodipeptide is coupled with the trifluoroacetate salt of the carboxylic acid substituted dipeptide.

13. The process of claim 1 comprising
(a) coupling an azaheterocyclyl pseudodipeptide of formula $$P_1\diagdown N\diagdown\diagdown\overset{O}{\diagdown}\underset{B}{\overset{}{N}}\diagdown\overset{}{\diagdown}\underset{O}{\overset{}{\diagdown}}\text{OH,}$$

or a base addition salt thereof, wherein
$P_1$ is a nitrogen protecting group; and
B is alkyl,
with a carboxylic acid substituted dipeptide of formula $$H_2N\diagdown\underset{CO_2Q_2}{\overset{O}{\diagdown}}\underset{H}{\overset{}{N}}\diagdown\underset{O}{\overset{J}{\diagdown}}L$$

or an acid addition salt thereof wherein
$Q_2$ is H or a carboxylic acid protecting group;
J is alkyl, cycloalkyl, or cycloalkylalkyl; and
L is $OR^1$ or $NR^1R^2$, where $R^1$ and $R^2$ are independently H, alkyl, cycloalkyl, cycloalkylalkyl, alkylcycloalkyl, alkylcycloalkylalkyl or aralkyl,
to prepare a pseudotetrapeptide of formula $$P_1\diagdown N\diagdown\diagdown\overset{O}{\diagdown}\underset{B}{\overset{}{N}}\diagdown\overset{}{\diagdown}\underset{O}{\overset{}{N}}\underset{CO_2Q_2}{\overset{H}{\diagdown}}\diagdown\underset{O}{\overset{J}{\diagdown}}L,$$

(b) optionally removing the nitrogen protecting group or carboxylic acid protecting group and
(c) optionally converting the pseudotetrapeptide to its salt or prodrug.

14. The process of claim 13 wherein $P_1$ is benzyloxycarbonyl and $Q_2$ is a benzyl.

15. The process of claim 13 wherein $P_1$ is benzyloxycarbonyl and $Q_2$ is H.

16. The process of claim 14 wherein B is ethyl, J is cyclohexylmethyl and L is $NH_2$.

17. The process of claim 15 wherein B is ethyl, J is cyclohexylmethyl and L is $NH_2$.

18. A process for preparing a cyclohexylmethyl substituted peptide of formula

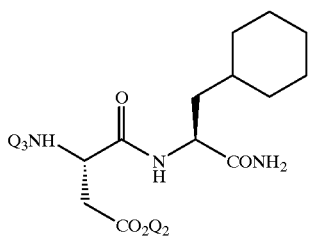

wherein

Q$_2$ is H or a carboxylic acid protecting group; and

Q$_3$ is H or a nitrogen protecting group; comprising (a) reducing a phenylmethyl substituted peptide of formula

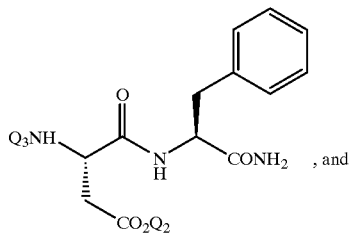

(b) optionally removing the nitrogen protecting group or carboxylic acid protecting group.

19. The process of claim 18 wherein the reducing is carried out by catalytic hydrogenation.

20. The process of claim 19 wherein the catalytic hydrogenation is carried out using a platinum catalyst.

21. The process of claim 20 wherein the platinum catalyst is platinum oxide or platinum on alumina.

22. A process for preparing an amido peptide of formula

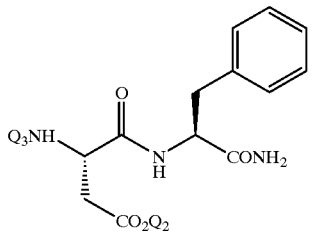

wherein

Q$_2$ is H or a base addition salt, or a carboxylic acid protecting group; and

Q$_3$ is H or a nitrogen protecting group; comprising amidating a peptide ester of formula

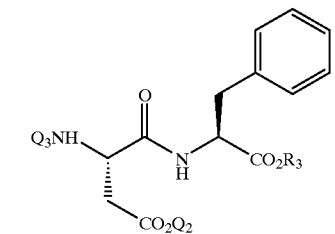

wherein R$_3$ is lower alkyl.

23. The process of claim 22 wherein the amidating is carried out using ammonia in alcohol.

24. The process of claim 23 wherein the alcohol is a lower alcohol.

25. The process of claim 23 wherein the amidating is carried out using ammonia in a lower alcohol-glycol solvent mixture.

26. The process of claim 25 wherein the lower alcohol-glycol solvent mixture comprises methanol and ethylene glycol.

27. A process for preparing a protected aspartame compound of formula

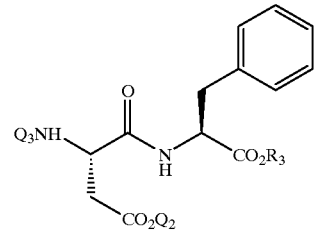

wherein

Q$_2$ is H or a carboxylic acid protecting group;

Q$_3$ is a nitrogen protecting group; and

R$_3$ is lower alkyl;

comprising introducing a N-protecting group to an aspartame compound of formula

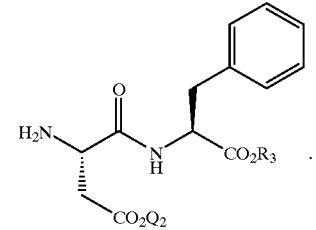

28. The process of claim 27 wherein Q$_3$ is benzyloxycarbonyl or t-butyloxycarbonyl.

29. The process of claim 28 wherein Q$_2$ is H.

30. A process for preparing an amido dipeptide of formula

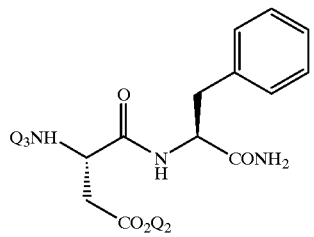

wherein $Q_3$ is a nitrogen protecting group; and
$Q^2$ is H, comprising (a) adding base and a N-protecting agent to a solution of aspartame in a solvent to form a solution of a compound of formula

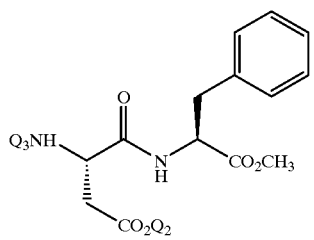

wherein $Q_2$ is H or a base addition salt, and (b) introducing ammonia into the resultant solution of step (a).

31. The process of claim 30 wherein $Q_3$ is tert-butyloxycarbonyl or benzyloxycarbonyl.

32. The process of claim 31 $Q_3$ is tert-butyloxycarbonyl.

33. The process of claim 32 wherein the solvent is alcohol.

34. The process of claim 33 wherein the alcohol is a lower alcohol or a lower alcohol-glycol mixture.

35. The process of claim 34 wherein the alcohol is methanol or a methanol-ethylene glycol mixture.

36. A process for preparing a cyclohexylmethyl substituted dipeptide of formula

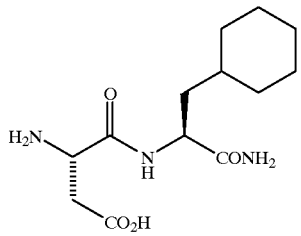

or an acid addition salt thereof, comprising (a) preparing a mixture of a catalyst and a phenylmethyl substituted peptide of formula

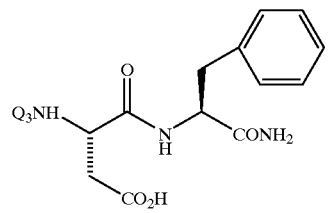

wherein $Q_3$ is tert-butyloxycarbonyl in a solvent, (b) treating the mixture with hydrogen,
(c) removing the catalyst from the mixture, and
(c) introducing gaseous HCl into the mixture.

37. The process of claim 36 wherein the solvent is acetic acid.

38. A process for preparing an azaheterocyclyl substituted acid compound of formula

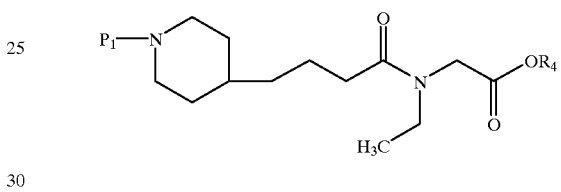

wherein $R_4$ is H or lower alkyl and
$P_1$ is a nitrogen protecting group, comprising (a) decarboxylating a 2-pyridylethyl-di-(lower alkyl) malonate of formula

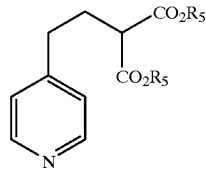

wherein $R_5$ is lower alkyl to prepare a pyridyl acid of formula

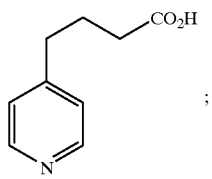

;

(b) hydrogenating the pyridyl acid with hydrogen in the presence of a catalyst to prepare a piperidine acid of formula

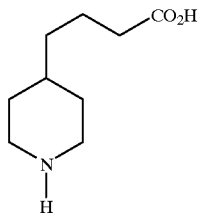

(c) optionally removing the catalyst;
(d) N-protecting the piperidine acid to prepare a nitrogen-protected piperidine acid of formula

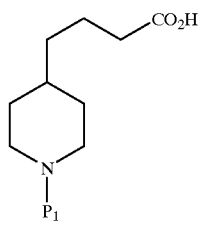

(e) coupling the nitrogen-protected piperidine acid with a N-ethylglycine compound of formula

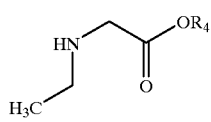

to prepare the azaheterocyclyl substituted acid compound; and (f) optionally deesterifing the azaheterocyclyl substituted acid compound wherein $R_4$ is lower alkyl.

39. The process of claim 38 wherein $P_1$ is benzyloxycarbonyl and $R_4$ is H.

40. The process of claim 39 wherein the decarboxylating is carried out by heating the 2-pyridylethyl-di-(lower alkyl) malonate in an aqueous acid solution.

41. The process of claim 40 wherein the aqueous acid is aqueous HCl.

42. The process of claim 39 wherein the hydrogenating is carried out in an aqueous acid solution.

43. The process claim 42 wherein the aqueous acid is aqueous HCl.

44. The process of claim 39 wherein the N-protecting is carried out in an aqueous base solution.

45. The process of claim 39 wherein
(a) a solution in aqueous acid of the 2-pyridylethyl-di-(lower alkyl) malonate is heated to prepare a solution of the pyridyl acid in aqueous acid;
(b) a catalyst is added to the solution of pyridyl acid and the mixture is treated with hydrogen to form a mixture of catalyst and the piperidine acid;
(c) the catalyst is separated from the mixture to prepare an aqueous solution of piperidine acid; and
(d) base and a N-protecting agent are added to the aqueous solution to prepare the N-protected piperidine acid.

46. The process of claim 45 wherein the aqueous acid is aqueous HCl.

47. A process for preparing a pseudotetrapeptide of formula

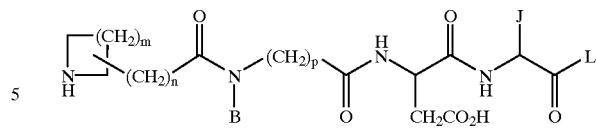

or a salt or prodrug thereof wherein
m is 3;
n is 2–6;
B is alkyl;
p is 1 or 2;
J is cyclohexylmethyl; and
L is $OR_1$ or $NR_1R_2$ wherein $R_1$ and $R_2$ are independently —H, alkyl, cycloalkyl, cycloalkylalkyl, alkylcycloalkyl, or alkylcycloalkylalkyl, comprising
(a) reducing a pseudotetrapeptide compound of formula

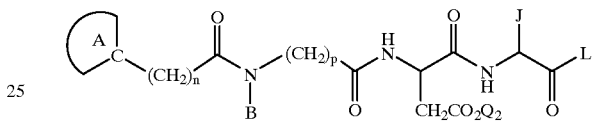

wherein

is pyridyl or

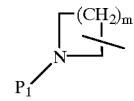

wherein m is 3 and $P_1$ is H or a nitrogen protecting group;
$Q_2$ is H or a carboxylic acid protecting group;
J is phenylmethyl;
(b) optionally removing the nitrogen protecting group or carboxylic acid protecting group; and
(c) optionally converting the pseudotetrapeptide to the salt or prodrug.

48. The process of claim 47 wherein the reducing is by catalytic hydrogenation.

49. The process of claim 48 wherein

is

wherein m is 3 and $P_1$ is a nitrogen protecting group;

n is 3;

p is 1; and $Q_2$ is a carboxylic acid protecting group.

50. The process of claim 49 wherein $P_1$ is a hydrogenation labile nitrogen protecting group; and $Q_2$ is a hydrogenation labile carboxylic acid protecting group.

51. The process of claim 50 wherein the catalytic hydrogenation effects simultaneous reduction and removal of $P_1$ and $Q_2$.

52. The process of claim 48 wherein

is pyridyl; and $Q_2$ carboxylic acid protecting group.

53. The process of claim 52 wherein $Q_2$ is a hydrogenation labile carboxylic acid protecting group.

54. The process of claim 53 wherein the catalytic hydrogenation effects simultaneous reduction and removal of $Q_2$.

55. A pseudodipeptide compound of formula

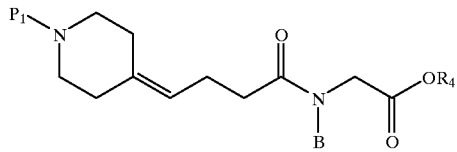

or a salt thereof wherein $P_1$ is H or a nitrogen protecting group;

B is alkyl, cycloalkyl, cycloalkylalkyl, alkylcycloalkyl, alkylcycloalkylalkyl, aryl, aralkyl, alkylaryl or alkylaralkyl; and $R_4$ is H or lower alkyl.

56. The pseudodipeptide compound of claim 55 wherein $P_1$ is a nitrogen protecting group, B is alkyl and $R_4$ is H.

57. The pseudodipeptide compound of claim 56 wherein $P_1$ is benzyloxycarbonyl and B is ethyl.

* * * * *